(12) United States Patent
Park et al.

(10) Patent No.: US 12,110,280 B2
(45) Date of Patent: Oct. 8, 2024

(54) AI ASSISTED CYCLIC CARBONATE MONOMER SYNTHESIS

(71) Applicant: International Business Machines Corporation, Armonk, NY (US)

(72) Inventors: Nathaniel H. Park, San Jose, CA (US); Victoria A Piunova, Los Gatos, CA (US); Dmitry Zubarev, San Jose, CA (US); Tim Erdmann, San Jose, CA (US); Pedro Arrechea, San Jose, CA (US); James L. Hedrick, Pleasanton, CA (US)

(73) Assignee: International Business Machines Corporation, Armonk, NY (US)

( * ) Notice: Subject to any disclaimer, the term of this patent is extended or adjusted under 35 U.S.C. 154(b) by 423 days.

(21) Appl. No.: 17/349,998

(22) Filed: Jun. 17, 2021

(65) Prior Publication Data
US 2023/0009671 A1    Jan. 12, 2023

(51) Int. Cl.
*C07D 319/04* (2006.01)
*C07D 273/02* (2006.01)
*C08G 64/16* (2006.01)

(52) U.S. Cl.
CPC ......... *C07D 319/04* (2013.01); *C07D 273/02* (2013.01); *C08G 64/1641* (2013.01)

(58) Field of Classification Search
CPC ............................ C07D 319/04; C07D 273/02
See application file for complete search history.

(56) References Cited

U.S. PATENT DOCUMENTS 8,361,396 B2   1/2013  Parker et al.
9,238,597 B2   1/2016  Burke et al.

OTHER PUBLICATIONS

Glaser et al. Proc. Nat. Acad. Sci. 1974, 71, 4072-4076 (Year: 1974).*
Hadjiivanov et al. Chem. Rev. 2021, 121, 1286-1424 (Year: 2021).*
Liu et al. J. Polym. Sci. Part A: Polym. Chem. 2003, 41, 4001-4006 (Year: 2003).*
Shields et al. Nature 2021, 590, 89-96 (Year: 2021).*
Hein, J. E. Nature 2021, 590, 40-41 (Year: 2021).*
Alves et al., "Organocatalytic Coupling of CO2 with Oxetane", Chemsuschem, DOI : 10.1002/cssc.201601185, 2017, 11 pages.
Brege et al., "The coupling of CO2 with diols promoted by organic dual systems: Towards products divergence via benchmarking of the performance metrics", Journal of $CO_2$ Utilization 38 (2020), 11 pages.
Reithofer et al., "Synthesis of cyclic carbonates with carbon dioxide and cesium carbonate", Green Chemistry, RSC Publishing, 2013, DOI: 10.1039/c3gc40790j, 5 pages.
McGuire et al., Synthesis of 5- to 8-membered cyclic carbonates from diols and CO2: A onestep, atmospheric pressure and ambient temperature procedure, Journal of $CO_2$ Utilization 27 (2018), 6 pages.
Buckley et al., "Selective Formation of Trimethylene Carbonate (TMC): Atmospheric Pressure Carbon Dioxide Utilization", Short Communication, Eur. J. Org. Chem. 2015, 5 pages.
Gregory et al.,Synthesis of 6-membered cyclic carbonates from 1,3-diols and low CO2 pressure: a novel mild strategy to replace phosgene reagents, RSC Advances, 2015, 5, 39404, 5 pages.
Gregory et al., "CO2-driven stereochemical inversion of sugars to create thymidine-based polycarbonates by ring-opening polymerisation", Polym. Chem., 2017, DOI: 10.1039/C7PY00118E, 10 pages.
Gregory et al., "Polymers from Sugars and CO2: Synthesis and Polymerization of a D-Mannose-Based Cyclic Carbonate", Macromolecules, ACS Pulblications, 2016, 5 pages.
Li et al., "Application of Artificial Neural Networks for Catalysis: A Review", Catalysts, MDPI, Published Oct. 18, 2017, 18 pages.
Martens et al., "Automated Synthesis of Monodisperse Oligomers, Featuring Sequence Control and Tailored Functionalization", ACS Publications, J. Am. Chem. Soc. 2016, 4 pages.
Wu et al., "Machine-learning-assisted discovery of polymers with high thermal conductivity using a molecular design algorithm", NPJ, Computational Materials, Published Online: Jun. 21, 2019, 11 pages.
Tan et al., "Towards Automated Monomer Synthesis: A Streamlined Approach for the Synthesis of Cyclic Carbonates", Institute of Bioengineering and Nanotechnology, IBM Research—Almaden, printed Mar. 23, 2021, 95 pages.

\* cited by examiner

*Primary Examiner* — Matthew P Coughlin
(74) *Attorney, Agent, or Firm* — Jeffrey M. Ingalls

(57) ABSTRACT

A method for synthesizing cyclic carbonate monomers using carbon dioxide ($CO_2$) is provided. The method also includes combining reagents to synthesize the cyclic carbonate monomer, the reagents including a substrate that is a 1,X-diol, where X is between 2 and 5, a base that is a tertiary amine, a promoter that is a multidentate, bis-tertiary amine base where nitrogens are separated by 2 to 4 carbon atoms, a solvent, and $CO_2$.

15 Claims, 13 Drawing Sheets

AI ASSISTED CYCLIC CARBONATE MONOMER SYNTHESIS

BACKGROUND

The present disclosure relates generally to the synthesis of cyclic carbonate monomers, and more specifically, to an artificial intelligence (AI) assisted synthesis of cyclic carbonate monomers and/or functionalized cyclic carbonate monomers from various diol monomers.

Aliphatic polycarbonates may be a polymer platform for precision biomedical applications. Their excellent biocompatibility and the broad scope of functional groups that may be incorporated on the polymer backbone have enabled a multitude of uses, such as antimicrobial, therapeutic, and/or high-performance materials. Of the many cyclic carbonate monomers reported, those derived from bis-methoxy propionic acid ("bis-MPA") can be versatile scaffolds. This is due to the sheer number of diverse functional groups that can be appended to the monomer. In turn, these functional groups impart unique properties to the resultant polymer, which can be principally accessed through controlled ring-opening polymerization. These enabling factors, in combination with the inexpensive and wide availability of the bis-MPA starting material, make this class of carbonates an ideal platform for the development of new applications for degradable materials with highly tailored properties.

The conversion of $CO_2$ into high-performance polymeric materials is an attractive strategy for economical utilization of $CO_2$ sequestered from point emission sources or direct air capture technology. Additionally, the ability to use $CO_2$ as a feedstock in the production of polymeric materials would also facilitate a shift in production away from the standard, fossil fuel-intensive approaches that utilized highly toxic chemicals such as phosgene. Achieving this requires new, highly efficient chemical transformations to be developed, refined, and scaled in order to ensure approach economic viability and carbon neutrality. Although $CO_2$ is an abundant and renewable feedstock, and since $CO_2$ is in its highest oxidation state, chemical transformations on $CO_2$ may require significant chemical innovation. Given the urgency with which the issue of climate change presents itself and the immense challenges of developing new methodologies for $CO_2$ conversion, there may be a need to dramatically accelerate research workflows for converting $CO_2$ to monomers that can be polymerized to make high-value polymeric materials.

SUMMARY

Embodiments of the present disclosure relate to a method for synthesizing cyclic carbonate monomers using carbon dioxide ($CO_2$). The method includes combining reagents to synthesize the cyclic carbonate monomer, the reagents including a substrate that is a 1,X-diol, where X is between 2 and 5, a base that is a tertiary amine, a promoter that is a multidentate, bis-tertiary amine base where the nitrogens are separated by 2 to 4 carbon atoms, a solvent, and $CO_2$.

Embodiments of the present disclosure relate to a computer implemented method for training an AI agent for cyclic carbonate monomer synthesis from carbon dioxide. The method includes pretraining a synthesis model with an AI agent based on historical monomer synthesis data. The method also includes selecting, based on the synthesis model, reagents to synthesize the cyclic carbonate monomer, the reagents including a substrate that is a 1,X-diol, where X is between 2 and 5, a base that is a tertiary amine, a promoter that is a multidentate, bis-tertiary amine base where the nitrogens are separated by 2 to 4 carbon atoms, a solvent, and $CO_2$. The method also includes identifying, based on the synthesis model, an experimental synthesis protocol. The method also includes selecting, based on the synthesis model, process operations for the cyclic carbonate monomer synthesis; executing the experimental synthesis protocol to generate the cyclic carbonate monomer. The method also includes collecting characterization data of results of the cyclic carbonate monomer synthesis for retraining of the synthesis model.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, explain the principles of the disclosure. The drawings are only illustrative of certain embodiments and do not limit the disclosure.

DETAILED DESCRIPTION

Figure 1:
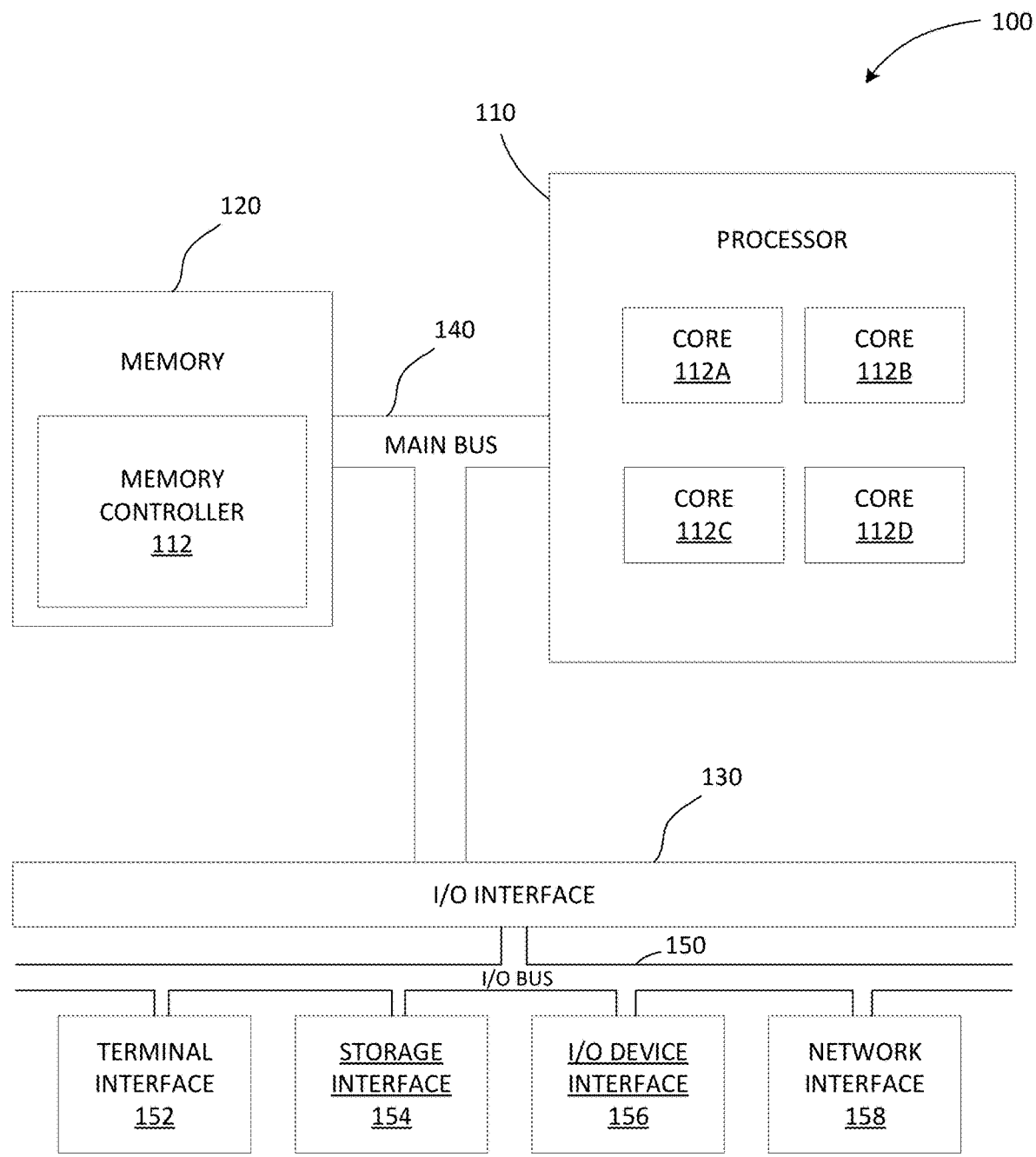
FIG. 1 depicts the representative major components of an example computer system that may be used, in accordance with some embodiments of the present disclosure.

The following detailed description is merely illustrative and is not intended to limit embodiments and/or application or uses of embodiments. One or more embodiments are now described with reference to the drawings, wherein like referenced numerals are used to refer to like elements throughout. In the following description, for purposes of explanation, numerous specific details are set forth in order to provide a more thorough understanding of one or more embodiments. It is evident, however, in various cases, that one or more embodiments can be practiced without these specific details.

For smaller-scale high-value specialty polycarbonates, potential applications include resins for 3D additive printing, macromonomers for polyurethanes, surfactants, biocompatible and degradable adhesives for medical applications. Enabling this potential, the last two decades have seen a renaissance in the synthesis of aliphatic carbonates driven by recent chemical advances. Monomers or polymers may be constructed from carbon dioxide instead of phosgene or other hazardous precursors. Further advances in chemistry have broadened the structural options in polycarbonate synthesis, facilitating advances in material design and discovery. Organometallic catalysts based on metals such as zinc, chromium, cobalt, and aluminum may react carbon dioxide with epoxides to form polycarbonate materials. Examples of supporting ligands may include alkoxides, porphyrins, salens, and carboxylates. Given the wide range of commercially functionalized epoxides or epoxide precursors, these synthetic protocols afford polycarbonates with a significant range of corresponding structural options. Similarly, advances in organic and organometallic catalysis for the ring-opening polymerization (ROP) of functionalized cyclic carbonates have significantly broadened the scope of materials available and potential application space.

Amongst the use cases for aliphatic polycarbonates, biomedical applications may benefit from a diverse choice of functional groups. Although there are over seven hundred 1,3-diols that can be transformed to 6-membered cyclic carbonates, the vast majority of reports employ 2,2-bis(hydroxymethyl) propionic acid (bis-MPA) as a precursor owing to the low cost and ease of functional group installation. For the case of bis-MPA, since the functionalized position is distal to the polymerization site, the ring-opening polymerization (ROP) conditions tend to be general. Similarly, inexpensive and readily available 1,5-diols may be exploited as precursors to functionalized 8-membered cyclic carbonates. Transformation of these functional monomers and subsequent polymers may be applied to numerous applications that include drug, gene, and cell delivery as well as the use of the polymer as a stand-alone therapeutic including antimicrobials, anticancer agents, and antiviral therapies packaged as micelles, hydrogels, or coacervates. Each one of these investigations may have an associated significant cost in terms of labor, time, and testing.

In the present embodiments, artificial intelligence (AI) and laboratory automation may disrupt traditional workflows by allowing for the rapid generation of suitable candidate materials. Advances in ROP catalysis have enabled automation capable of generating polymer libraries augmented by recommender systems. Nonetheless, monomer synthesis may remain as a bottleneck to advanced materials and biologics discovery, as these are often complex and multiple-step syntheses. Moreover, automation of some or all of the steps has either been not explored or sufficiently developed.

There are numerous synthetic methods to functionalize 6-, 7- and 8-membered cyclic carbonate monomers, and many of these synthetic methods may be derived from Bis-MPA (Scheme SI-1). For a given desired functional group, these methods generally entail two to five steps depending on the availability of the corresponding halide or alcoholic precursor. Some methods require protection/deprotection steps to accomplish the monomer synthesis (Scheme SI-1a and b). Moreover, many of these synthesis routes employ the use of undesirable phosgene or equivalents to affect the cyclization. To avoid these downsides, alternative strategies may use pentafluorophenyl carbonate to afford a two-step approach to cyclic carbonates (Scheme SI c). Similarly, the use of 3 equivalents of N,N-carbonyldiimidazole (CDI), followed by a concerted cyclization esterification reaction in the presence of alcohol, afforded the targeted cyclic carbonated in two steps. Cyclic carbonates may also be synthesized in two high-yielding steps involving either 1) alkylation followed by cyclization (CDI) or 2) cyclization (CDI) followed by esterification (Scheme SI-1e and f). Since the formation of carbonate compounds derived from carbon dioxide is a method of carbon sequestration and storage, the use of this precursor is a challenge that is being addressed via catalysis.

The present embodiments may achieve a significant reduction in the time and the cost of materials discovery together with the concomitant increase in the rate to generate materials libraries. The present embodiments aim to disrupt current workflows through chemical innovation, automation or partial automation, and the employment of artificial intelligence (AI) systems. The present embodiments may allow for the discovery of macromolecular therapeutics and drug delivery assemblies, where the critical bottleneck of functional monomer synthesis may be addressed. In certain of the present embodiments, 1, 3- and 1, 5-diols are employed (more generally, a diol that is a 1,X-diol, where X is between 2 and 5), as described above, in a streamlined two-step process, where the functionality is introduced by alkyl halides or alcohols without the use of protection/deprotection strategies. In addition, the present embodiments may include catalyst development that enables clean (minimal oligomerization) and high yielding ring-closing to yield the desired carbonate while dramatically reducing reaction times. In certain embodiments, the catalyst (or promoter) is selected from the group consisting of TMEDA, PDMEA, and HMTEA. In general, a catalyst is a substance that increases the rate of a chemical reaction without itself being changed at the end of the chemical reaction. On the other hand, a promoter is a material that enhances the action of a catalyst without actually having any catalytic value itself. In certain examples, the reactions schema may include a catalyst or a promoter, or a combination of the two. These chemical advancements allowed these transformations to be automated, requiring integrated custom hardware and software. Therefore, the present embodiments describe an expedited route to the generation of libraries of functional 6- and 8-membered cyclic carbonate monomers using an AI assisted approach.

FIG. 1 depicts the representative major components of an example computer system 100 (alternatively, computer) that may be used, in accordance with some embodiments of the present disclosure. It is appreciated that individual components may vary in complexity, number, type, and/or configuration. The particular examples disclosed are for example purposes only and are not necessarily the only such variations. The computer system 100 may include a processor 110, memory 120, an input/output interface (herein I/O or I/O interface) 130, and a main bus 140. The main bus 140 may provide communication pathways for the other components of the computer system 100. In some embodiments, the main bus 140 may connect to other components such as a specialized digital signal processor (not depicted).

The processor 110 of the computer system 100 may be comprised of one or more cores 112A, 112B, 112C, 112D (collectively 112). The processor 110 may additionally include one or more memory buffers or caches (not depicted) that provide temporary storage of instructions and data for the cores 112. The cores 112 may perform instructions on input provided from the caches or from the memory 120 and output the result to caches or the memory. The cores 112 may be comprised of one or more circuits configured to perform one or more methods consistent with embodiments of the present disclosure. In some embodiments, the computer system 100 may contain multiple processors 110. In some embodiments, the computer system 100 may be a single processor 110 with a singular core 112.

The memory 120 of the computer system 100 may include a memory controller 122. In some embodiments, the memory 120 may include a random-access semiconductor memory, storage device, or storage medium (either volatile or non-volatile) for storing data and programs. In some embodiments, the memory may be in the form of modules (e.g., dual in-line memory modules). The memory controller 122 may communicate with the processor 110, facilitating storage and retrieval of information in the memory 120. The memory controller 122 may communicate with the I/O interface 130, facilitating storage and retrieval of input or output in the memory 120.

The I/O interface 130 may include an I/O bus 150, a terminal interface 152, a storage interface 154, an I/O device interface 156, and a network interface 158. The I/O interface 130 may connect the main bus 140 to the I/O bus 150. The I/O interface 130 may direct instructions and data from the processor 110 and memory 120 to the various interfaces of the I/O bus 150. The I/O interface 130 may also direct instructions and data from the various interfaces of the I/O bus 150 to the processor 110 and memory 120. The various interfaces may include the terminal interface 152, the storage interface 154, the I/O device interface 156, and the network interface 158. In some embodiments, the various interfaces may include a subset of the aforementioned interfaces (e.g., an embedded computer system in an industrial application may not include the terminal interface 152 and the storage interface 154).

Logic modules throughout the computer system 100—including but not limited to the memory 120, the processor 110, and the I/O interface 130—may communicate failures and changes to one or more components to a hypervisor or operating system (not depicted). The hypervisor or the operating system may allocate the various resources available in the computer system 100 and track the location of data in memory 120 and of processes assigned to various cores 112. In embodiments that combine or rearrange elements, aspects and capabilities of the logic modules may be combined or redistributed. These variations would be apparent to one skilled in the art.

Figure 2:
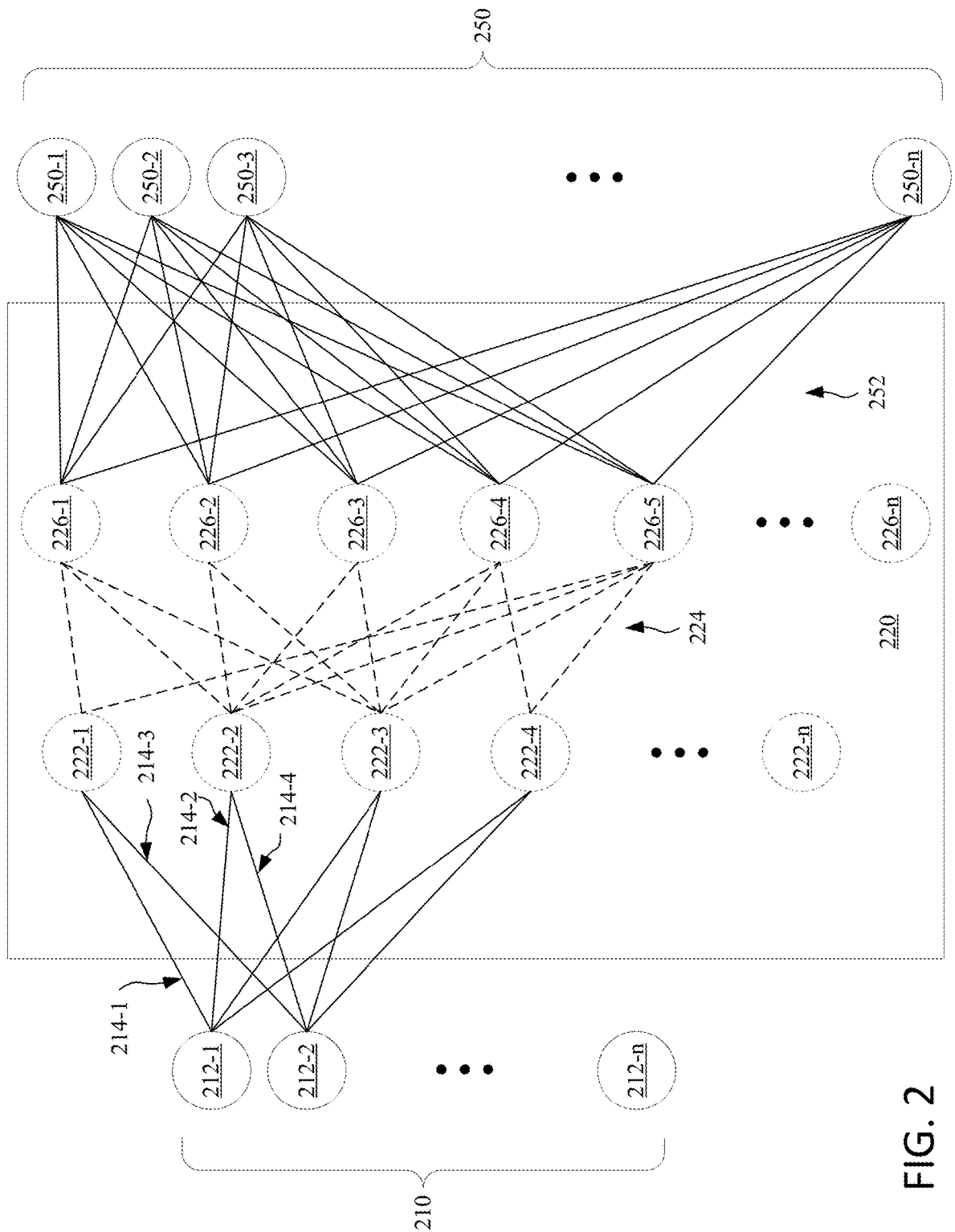
FIG. 2 depicts an example neural network representative of one or more artificial neural networks capable performing one or more operations of automated monomer synthesis from $CO_2$, consistent with embodiments of the present disclosure.

FIG. 2 depicts an example neural network (alternatively, "network") 200 representative of one or more artificial neural networks capable of assisting with the generation of libraries of functional 6- and 8-membered cyclic carbonate monomers using $CO_2$, consistent with embodiments of the present disclosure. The neural network 200 is made up of a plurality of layers. The network 200 includes an input layer 210, a hidden section 220, and an output layer 250. Though network 200 depicts a feed-forward neural network, it should be appreciated that other neural network layouts may also be configured to perform functional monomer synthesis and the generation of libraries of functional 6- and 8-membered cyclic carbonate monomers, such as a recurrent neural network layout (not depicted). In some embodiments, the network 200 may be a design-and-run neural network, and the layout depicted may be created by a computer programmer. In some embodiments, the network 200 may be a design-by-run neural network, and the layout depicted may be generated by the input of data and by the process of analyzing that data according to one or more defined heuristics. The network 200 may operate in a forward propagation by receiving an input and outputting a result of the input. The network 200 may adjust the values of various components of the neural network by backward propagation (backpropagation).

The input layer 210 includes a series of input neurons 212-1, 212-2, up to 212-n (collectively, 212) and a series of input connections 214-1, 214-2, 214-3, 214-4, etc. (collectively, 214). The input layer 210 represents the input from data that the neural network is supposed to analyze (e.g., functional monomer synthesis and the generation of libraries of functional 6- and 8-membered cyclic carbonate monomers). Each input neuron 212 may represent a subset of the input data. For example, the neural network 200 is provided with one or more monomer synthesis reaction conditions (e.g., the target monomer, catalyst and or base combinations, reaction time, temperature, molarity, solvent, order of addition of reaction components, evaluated cost of goods, conversion of a diol to carbonate without oligomerization, TsCl stoichiometry, tetramethylethylenediamine (TMEDA) stoichiometry, stoichiometry of a diol to a base to TsCl, additional related bases, stoichiometry of bis methiopropamine (MPA), N,N-diisopropylethylamine (DIEA) and benzyl bromide, rates of addition of reaction components, rates of removal of reaction components, solvent type(s), monomer substrate type, amount of base relative to substrate type, reaction temperature(s), the concentration of the diol, amount of catalyst or promoter relative to the substrate, etc.), wherein the reaction condition is represented by a particular input neuron 212.

In another example, input neuron 212-1 may be a first monomer synthesis reaction condition, input neuron 212-2 may be a second monomer synthesis reaction condition, etc. The number of input neurons 212 may correspond to the size of the input. The number of input neurons 212 may also correspond to the type of input. The type of input neurons 212 may correspond to the type of input.

The input connections 214 represent the output of the input neurons 212 to the hidden section 220. Each of the input connections 214 varies depending on the value of each input neuron 212 and based upon a plurality of weights (not depicted). For example, the first input connection 214-1 has a value that is provided to the hidden section 220 based on the input neuron 212-1 and a first weight. Continuing the example, the second input connection 214-2 has a value that is provided to the hidden section 220 based on the input neuron 212-1 and a second weight. Further continuing the example, the third input connection 214-3 based on the input neuron 212-2 and a third weight, etc. Alternatively stated, the input connections 214-1 and 214-2 share the same output component of input neuron 212-1 and the input connections 214-3 and 214-4 share the same output component of input neuron 212-2; all four input connections 214-1, 214-2, 214-3, and 214-4 may have output components of four different weights. Though the neural network 200 may have different weightings for each connection 214, some embodiments may contemplate weights that are similar. In some embodiments, each of the values of the input neurons 212 and the connections 214 may necessarily be stored in memory.

The hidden section 220 includes one or more layers that receive inputs and produce outputs. The hidden section 220 includes a first hidden layer of calculation neurons 222-1, 222-2, 222-3, 222-4, up to 222-$n$ (collectively, 222); a second hidden layer of calculation neurons 226-1, 226-2, 226-3, 226-4, 226-5, up to 226-$n$ (collectively 226); and a series of hidden connections 224 coupling the first hidden layer and the second hidden layer. It should be appreciated that neural network 200 only depicts one of many neural networks capable of one or more operations of related to monomer synthesis and the generation of libraries of functional 6- and 8-membered cyclic carbonate monomers consistent with some embodiments of the disclosure. Consequently, the hidden section 220 may be configured with more or less hidden layers (e.g., one hidden layer, seven hidden layers, twelve hidden layers, etc.)—two hidden layers are depicted for example purposes.

The first hidden layer 222 includes the calculation neurons 222-1, 222-2, 222-3, 222-4, up to 222-$n$. Each calculation neuron of the first hidden layer 222 may receive as input one or more of the connections 214. For example, calculation neuron 222-1 receives input connection 214-1 and input connection 214-2. Each calculation neuron of the first hidden layer 222 also provides an output. The output is represented by the dotted lines of hidden connections 224 flowing out of the first hidden layer 222. Each of the calculation neurons 222 performs an activation function during forward propagation. In some embodiments, the activation function may be a process of receiving several binary inputs, and calculating a single binary output (e.g., a perceptron). In some embodiments, the activation function may be a process of receiving several non-binary inputs (e.g., a number between 0 and 1, .671, etc.) and calculating a single non-binary output (e.g., a number between 0 and 1, a number between −0.5 and 0.5, etc.). Various functions may be performed to calculate the activation function (e.g., a sigmoid neurons or other logistic functions, tanh neurons, softplus functions, softmax functions, rectified linear units, etc.). In some embodiments, each of the calculation neurons 222 also contains a bias (not depicted). The bias may be used to decide the likelihood or valuation of a given activation function. In some embodiments, each of the values of the biases for each of the calculation neurons must necessarily be stored in memory.

The neural network 200 may include the use of a sigmoid neuron for the activation function of calculation neuron 222-1. An equation (Equation 1, stated below) may represent the activation function of calculation neuron 212-1 as f(neuron). The logic of calculation neuron 222-1 may be the summation of each of the input connections that feed into calculation neuron 222-1 (i.e., input connection 214-1 and input connection 214-3) which are represented in Equation 1 as j. For each j the weight w is multiplied by the value x of the given connected input neuron 212. The bias of the calculation neuron 222-1 is represented as b. Once each input connection j is summed the bias b is subtracted. Finalizing the operations of this example as follows: given a larger positive number of results from the summation and bias in activation f(neuron), the output of calculation neuron 222-1 approaches approximately 1; given a larger negative number of results from the summation and bias in activation f(neuron), the output of calculation neuron 222-1 approaches approximately 0; and given a number somewhere in between a larger positive number and a larger negative number of results from the summation and bias in activation f(neuron), the output varies slightly as the weights and biases vary slightly.

$$f(\text{neuron}) = \frac{1}{1 + \exp\left(-\sum_j w_j x_j - b\right)} \qquad \text{Equation 1}$$

The second hidden layer 226 includes the calculation neurons 226-1, 226-2, 226-3, 226-4, 226-5, up to 226-$n$. In some embodiments, the calculation neurons of the second hidden layer 226 may operate similarly to the calculation neurons first hidden layer 222. For example, the calculation neurons 226-1 to 226-$n$ may each operate with a similar activation function as the calculation neurons 222-1 to 222-$n$. In some embodiments, the calculation neurons of the second hidden layer 226 may operate differently to the calculation neurons of the first hidden layer 222. For example, the calculation neurons 226-1 to 226-$n$ may have a first activation function, and the calculation neurons 222-1 to 222-$n$ may have a second activation function.

Similarly, the connectivity to, from, and between the various layers of the hidden section 220 may also vary. For example, the input connections 214 may be fully connected to the first hidden layer 222 and hidden connections 224 may be fully connected from the first hidden layer to the second hidden layer 226. In some embodiments, fully connected may mean that each neuron of a given layer may be connected to all the neurons of a previous layer. In some embodiments, fully connected may mean that each neuron of a given layer may function completely independently and may not share any connections. In a second example, the input connections 214 may not be fully connected to the first hidden layer 222 and the hidden connections 224 may not be fully connected from the first hidden layer to the second hidden layer 226.

Further, the parameters to, from, and between the various layers of the hidden section 220 may also vary. In some embodiments, the parameters may include the weights and the biases. In some embodiments, there may be more or fewer parameters than the weights and biases. For purposes of example, neural network 200 may be in the form of a convolutional neural network or convolution network. The convolutional neural network may include a sequence of heterogeneous layers (e.g., an input layer 210, a convolution layer 222, a pooling layer 226, and an output layer 250). In such a network, the input layer may hold the raw pixel data of an image in a 3-dimensional volume of width, height, and color. The convolutional layer of such a network may output from connections that are only local to the input layer to identify a feature in a small section of the image (e.g., an eyebrow from a face of a first subject in a picture depicting four subjects, a front fender of a vehicle in a picture depicting a truck, etc.). Given this example, the convolutional layer may include weights and biases, as well as additional parameters (e.g., depth, stride, and padding). The pooling layers of such a network may take as input the output of the convolutional layers but perform a fixed function operation (e.g., an operation that does not take into account any weight or bias). Also, given this example, the pooling layer may not contain any convolutional parameters and may also not contain any weights or biases (e.g., performing a down-sampling operation).

The output layer 250 includes a series of output neurons 250-1, 250-2, 250-3, up to 250-$n$ (collectively, 250). The output layer 250 holds a result of the analysis of the neural network 200. In some embodiments, the output layer 250 may be a categorization layer used to identify a feature of the input to the network 200. For example, the network 200 may be a classification network trained to identify Arabic numerals. In such an example, the network 200 may include ten output neurons 250 corresponding to which Arabic numeral the network has identified (e.g., output neuron 250-2 having a higher activation value than output neurons 250 may indicate the neural network determined an image contained the number '1'). In some embodiments, the output layer 250 may be a real-value target (e.g., trying to predict a result when an input is a previous set of results), and there may be only a singular output neuron (not depicted). The output layer 250 is fed from an output connection 252. The output connection 252 provides the activations from the hidden section 220. In some embodiments, the output connections 252 may include weights, and the output neurons 250 may include biases.

Training the neural network depicted by neural network 200 may include performing backpropagation. Backpropagation is different from forward propagation. Forward propagation may include feeding of data into the neurons of input layer 210; performing the calculations of the connections 214, 224, 252; and performing the calculations of the calculation neurons in layers 222 and 226. The forward propagation may also be the layout of a given neural network (e.g., recurrence, number of layers, number of neurons in one or more layers, layers being fully connected or not to other layers, etc.). Backpropagation may be used to determine an error of the parameters (e.g., the weights and the biases) in the network 200 by starting with the output neurons 250 and propagating the error backward through the various connections 252, 224, 214 and layers 226, 222, respectively.

Backpropagation includes performing one or more algorithms based on one or more training data to reduce the difference between what a given neural network determines from an input and what the given neural network should determine from the input. The difference between a network determination and the correct determination may be called the objective function (alternatively, the cost function). When a given neural network is initially created, and data is provided and calculated through a forward propagation, the result or determination may be an incorrect determination. For example, the neural network may perform a backpropagation that may alter the values of the weights of connections 214, 224, and 252; and may alter the values of the biases of the calculation neurons of first hidden layer 222, the calculation neurons of second hidden layer 226, and the output neurons of output layer 250.

Equation 2 provides an example of the objective function ("example function") in the form of a quadratic cost function (e.g., mean squared error)—other functions may be selected, and the mean squared error is selected, for example purposes. In Equation 2, all of the weights may be represented by w, and biases may be represented by b of neural network 200. The network 200 is provided a given number of training inputs n in a subset (or entirety) of training data that have input values x. The network 200 may yield output a from x and should yield a desired output y(x) from x. Backpropagation or training of the network 200 should be a reduction or minimization of the objective function 'O(w,b)' via alteration of the set of weights and biases. Successful training of network 200 should not only include the reduction of the difference between the answer a and the correct answers y(x) for the input values x, but given new input values (e.g., from additional training data, from validation data, etc.).

$$O(w, b) \equiv \frac{1}{2n} \sum_{x} \|y(x) - a\|^2 \qquad \text{Equation 2}$$

Many options may be utilized for backpropagation algorithms in both the objective function (e.g., mean squared error, cross-entropy cost function, accuracy functions, confusion matrix, precision-recall curve, mean absolute error, etc.) and the reduction of the objective function (e.g., gradient descent, batch-based stochastic gradient descent, Hessian optimization, momentum-based gradient descent, etc.). Backpropagation may include using a gradient descent algorithm (e.g., computing partial derivatives of an objective function in relation to the weights and biases for all of the training data). Backpropagation may include determining a stochastic gradient descent (e.g., computing partial derivatives of a subset the training inputs in a subset or batch of training data). Additional parameters may be involved in the various backpropagation algorithms (e.g., the learning rate for the gradient descent). Large alterations of the weights and biases through backpropagation may lead to incorrect training (e.g., overfitting to the training data, reducing towards a local minimum, reducing excessively past a global minimum, etc.). Consequently, modification to objective functions with more parameters may be used to prevent incorrect training (e.g., utilizing objective functions that incorporate regularization to prevent overfitting). Also, consequently, the alteration of the neural network 200 may be small in any given iteration. Backpropagation algorithms may need to be repeated for many iterations to perform accurate learning as a result of the necessitated smallness of any given iteration.

For example, neural network 200 may have untrained weights and biases, and backpropagation may involve the stochastic gradient descent to train the network over a subset of training inputs (e.g., a batch of 10 training inputs from the entirety of the training inputs). Continuing the example, network 200 may continue to be trained with a second subset of training inputs (e.g., a second batch of 10 training input from the entirety other than the first batch), which can be repeated until all of the training inputs have been used to calculate the gradient descent (e.g., one epoch of training data). Stated alternatively, if there are 10,000 monomer synthesis reaction input conditions in total, and one iteration of training uses a batch size of 100 training inputs, 1,000 iterations would be needed to complete an epoch of the training data. Many epochs may be performed to continue training of a neural network. There may be many factors that determine the selection of the additional parameters (e.g., larger batch sizes may cause improper training, smaller batch sizes may take too many training iterations, larger batch sizes may not fit into memory, smaller batch sizes may not take advantage of discrete GPU hardware efficiently, too little training epochs may not yield a fully trained network, too many training epochs may yield overfitting in a trained network, etc.). Further, network 200 may be evaluated to quantify the performance of evaluating a dataset, such as by use of an evaluation metric (e.g., mean squared error, cross-entropy cost function, accuracy functions, confusion matrix, precision-recall curve, mean absolute error, etc.).

In some embodiments, the method of performing automated monomer synthesis from carbon dioxide may execute machine learning on data using one or more of the following example techniques: K-nearest neighbor (KNN), learning vector quantization (LVQ), self-organizing map (SOM), logistic regression, ordinary least squares regression (OLSR), linear regression, stepwise regression, multivariate adaptive regression spline (MARS), ridge regression, least absolute shrinkage and selection operator (LASSO), elastic net, least-angle regression (LARS), probabilistic classifier, naïve Bayes classifier, binary classifier, linear classifier, hierarchical classifier, canonical correlation analysis (CCA), factor analysis, independent component analysis (ICA), linear discriminant analysis (LDA), multidimensional scaling (MDS), non-negative metric factorization (NMF), partial least squares regression (PLSR), principal component analysis (PCA), principal component regression (PCR), Sammon mapping, t-distributed stochastic neighbor embedding (t-SNE), bootstrap aggregating, ensemble averaging, gradient boosted decision tree (GBRT), gradient boosting machine (GBM), inductive bias algorithms, Q-learning, state-action-reward-state-action (SARSA), temporal difference (TD) learning, apriori algorithms, equivalence class transformation (ECLAT) algorithms, Gaussian process regression, gene expression programming, group method of data handling (GMDH), inductive logic programming, instance-based learning, logistic model trees, information fuzzy networks (IFN), hidden Markov models, Gaussian naïve Bayes, multinomial naïve Bayes, averaged one-dependence estimators (AODE), Bayesian network (BN), classification and regression tree (CART), chi-squared automatic interaction detection (CHAID), expectation-maximization algorithm, feedforward neural networks, logic learning machine, self-organizing map, single-linkage clustering, fuzzy clustering, hierarchical clustering, Boltzmann machines, convolutional neural networks, recurrent neural networks, hierarchical temporal memory (HTM), and/or other machine learning techniques.

In certain embodiments, the system utilizes two key platforms of commercially available and synthetic 1,3- and 1,5-diols to generate 6- and 8-membered cyclic carbonates in a two-step process that includes an alkylation of the scaffold step and an aqueous extraction step.

In certain embodiments, bis-MPA (see e.g., diol monomer 302 in FIG. 3A) is chosen as the key scaffold for the synthesis of the functional 1,3-diols owing to the cost, availability and the ease of functional group installation. However, it should be appreciated that any suitable scaffold (s) other than bis-MPA may be used for the synthesis of the functional 1,3-diols. In certain embodiments, Fisher esterification or alkylation of the carboxylic acid group is used to install the functional group in the presence of diisopropylethyl amine in acetonitrile. In certain examples, the diols are isolated by a simple aqueous extraction (e.g., 1M HCl, brine) in ethyl acetate, concentrated and used without further purification. In certain examples, a diverse range of functional groups are installed to modulate the hydrophobicity/hydrophilicity or glass transition temperature, installation of protected carboxylic acid groups or functional groups amenable towards post-polymerization modification as well as structure-directing agents.

Similarly, in certain embodiments, diethanolamine (see e.g., diol monomer 402 in FIG. 4A) is chosen as the key platform for the synthesis of functional 1,5-diols. In certain embodiments, alkylation is accomplished in acetonitrile in the presence of excess potassium carbonate (80° C.). In embodiments, a number of alkyl halides are surveyed as a means to install diverse functional groups.

In certain embodiments, in a second step of the process of producing the compounds (i.e., the functional 1,3-diols and the functional 1,5-diols), the compounds are purified by a simple aqueous extraction (ethyl acetate), and selected compounds may require recrystallization (e.g., using ethyl acetate/hexane).

Figure 3A:
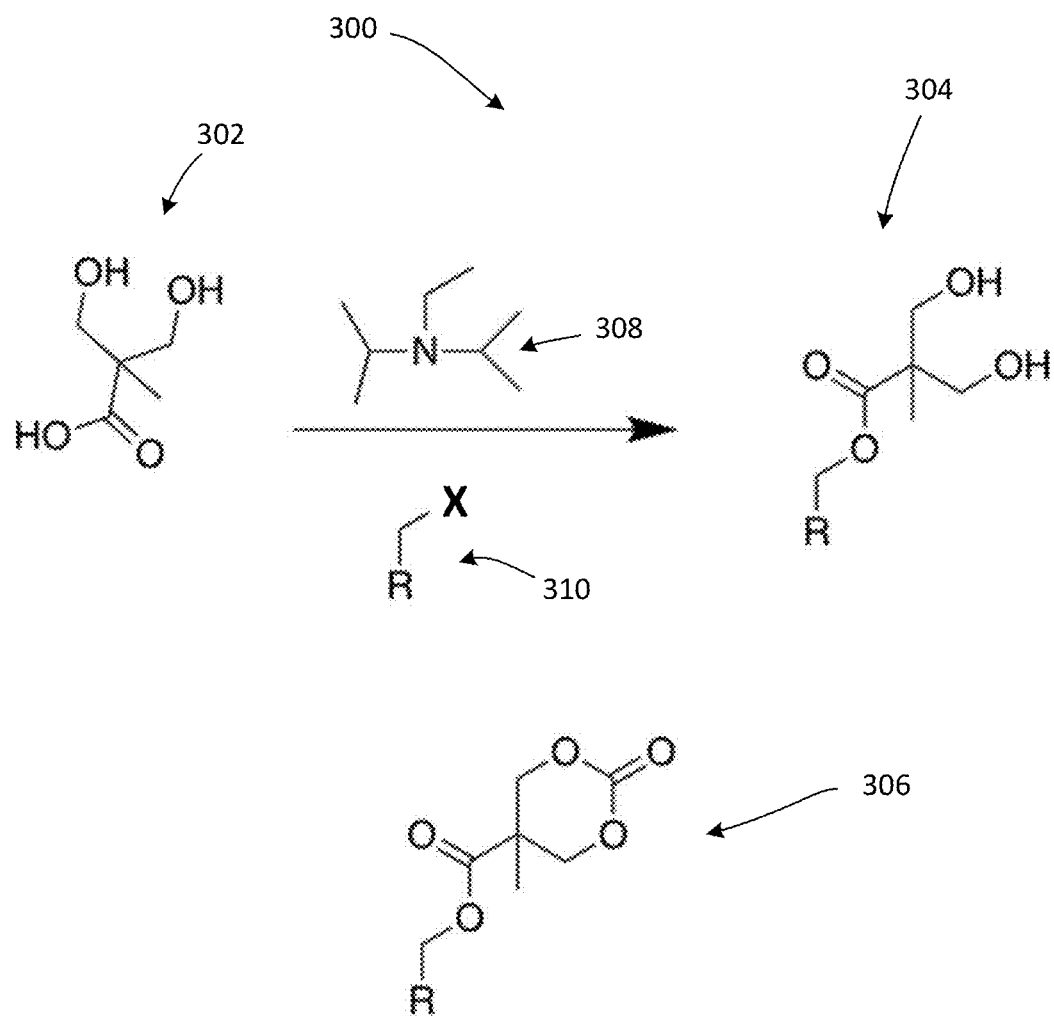
FIG. 3A illustrates a diagram of an example, non-limiting alkylation scheme that can be comprised within an alkylation-cyclization process for the synthesis of cyclic carbonate monomers in accordance with one or more embodiments described herein.

FIG. 3A illustrates a diagram of an example, non-limiting alkylation scheme 300 that can be performed during one or more alkylation-cyclization processes to facilitate synthesis of one or more functionalized cyclic carbonate monomers 306 (functional 1,3-diols) in accordance with one or more embodiments described herein. Repetitive description of like elements employed in other embodiments described herein is omitted for sake of brevity.

FIG. 3A depicts the exemplary alkylation scheme 300 with regards to bis-MPA as the diol monomer 302. However, as described herein, the use of other monomers as the diol monomer 302 is also envisaged. Alkylation scheme 300 exemplifies how one or more diol monomers 302 can undergo an alkylation to form one or more generic functionalized diol monomers 304. As shown in FIG. 3A, during alkylation, the carboxyl group of the diol monomer 302 (e.g., bis-MPA) can be selectively alkylated. In various embodiments, the alkylation can be facilitated by one or more organic amine bases and one or more solvents. Example organic amine bases that can be utilized in the alkylation scheme 300 can include, but are not limited to: triethylamine ("Et3N"), diisopropylethylamine ("DIEA"), 1,1,3,3-tetramethylguanidine, 1,8-diazabicyclo(5.4.0)undec-7-ene, 1,5-diazabicyclo(4.3.0)non-5-ene, 2-tert-butyl-1,1,3,3-tetramethylguanidine, N,N-dicyclohexylmethylamine, N,Ndiethylmethylamine, a combination thereof, and/or the like. Example solvents that can be utilized in the alkylation scheme 300 can include, but are not limited to: acetonitrile ("MeCN"), ethyl acetate, acetone, butyl acetate, isopropyl acetate, N,N-dimethylformamide, N,Ndimethylacetamide, dimethyl sulfoxide, N-methyl-2-pyrrolidone, N-cyclohexyl-2-pyrrolidone, cyclohexanone, dichloroethane, propylene carbonate, tetrahydrofuran, cyclopentyl methyl ether, dimethoxy ethane, a combination thereof, and/or the like. As shown in the example of FIG. 3A, the alkylation of the carboxylic acid group was used to install the functional group (—R) (i.e., in functional group substrate 310) in the presence of diisopropylethyl amine 308 in acetonitrile. In certain examples, the alkylation scheme 300 can be performed at room temperature ("RT") and/or at an elevated temperature ("A").

For example, the one or more amine bases can enable functionalization of the one or more diol monomers 302 with one or more substrates (e.g., functional group substrate 310) having a reactive functional group (e.g., alkyl, benzylic, or allylic halides and/or alcohols). For instance, the one or more substrates 310 having a reactive functional group (e.g., alkyl, benzylic, or allylic halides and/or alcohols) can be represented by "R—X" in FIG. 3A; wherein "R" can represent one or more reactive functional groups (e.g., alkyl groups, benzyl groups, and/or allylic groups) that can become pendent functional groups as a result of the functionalization. Also, "X" can represent one or more halides, sulfonates, carbonates, esters, carbamates, phosphonates, and/or hydroxyl groups. Example substrates with reactive functional groups (e.g., represented by "R—X" in FIG. 3A) that can functionalize the one or more diol monomers 104 can include, but are not limited to: α,α'-dichloro-p-xylene, benzyl bromide, pentafluorobenzyl bromide, tert-butyl chloroacetate, ethanol, 1-bromooctane, 1-bromododecane, 2-(2-(2-methoxyethoxy)ethoxy)ethyl 4-methylbenzenesulfonate, 1-iodobutane, 2-bromopropane, tert-butyl 4-(bromomethyl)benzoate, a combination thereof, and/or the like.

The following experimental procedure can exemplify implementation of the alkylation scheme 300. A flask can be equipped with a magnetic stir-bar and charged with bis-MPA (e.g., 1 equivalent) and MeCN (e.g., 0.5 molar (M)). The suspension can be stirred at room temperature and DIEA (e.g., 1.05 equivalents) can be added. The reaction mixture can be stirred until becomes completely homogenous (e.g., about 5 minutes) and the alkylating agent is added (e.g., 1 equivalent). The flask can be equipped with a reflux condenser and heated to the indicated temperature in a pre-heated oil bath until the reaction has reached full conversion as determined by $^1$H NMR (i.e., proton nuclear magnetic resonance) analysis of the crude reaction mixture. Once complete, the reaction mixture may be removed from the oil bath and allowed to cool to room temperature. The solvent can then be removed with the aid of the rotary evaporator and the crude residue can be dissolved in, for example, ethyl acetate ("EtOAc") (e.g., 50 mL) and poured into 1 M hydrochloric acid ("HCl") (e.g., 100 mL). The phases may be separated, and the aqueous layer can be extracted twice more with EtOAc (e.g., 50 mL). The combined organic layers can be dried over magnesium sulfate ("MgSO$_4$"), filtered, and concentrated with the aid of a rotary evaporator. It should be appreciated that this is only one example reaction scheme, and any other suitable procedure can exemplify implementation of the alkylation scheme 300.

Figure 3B:
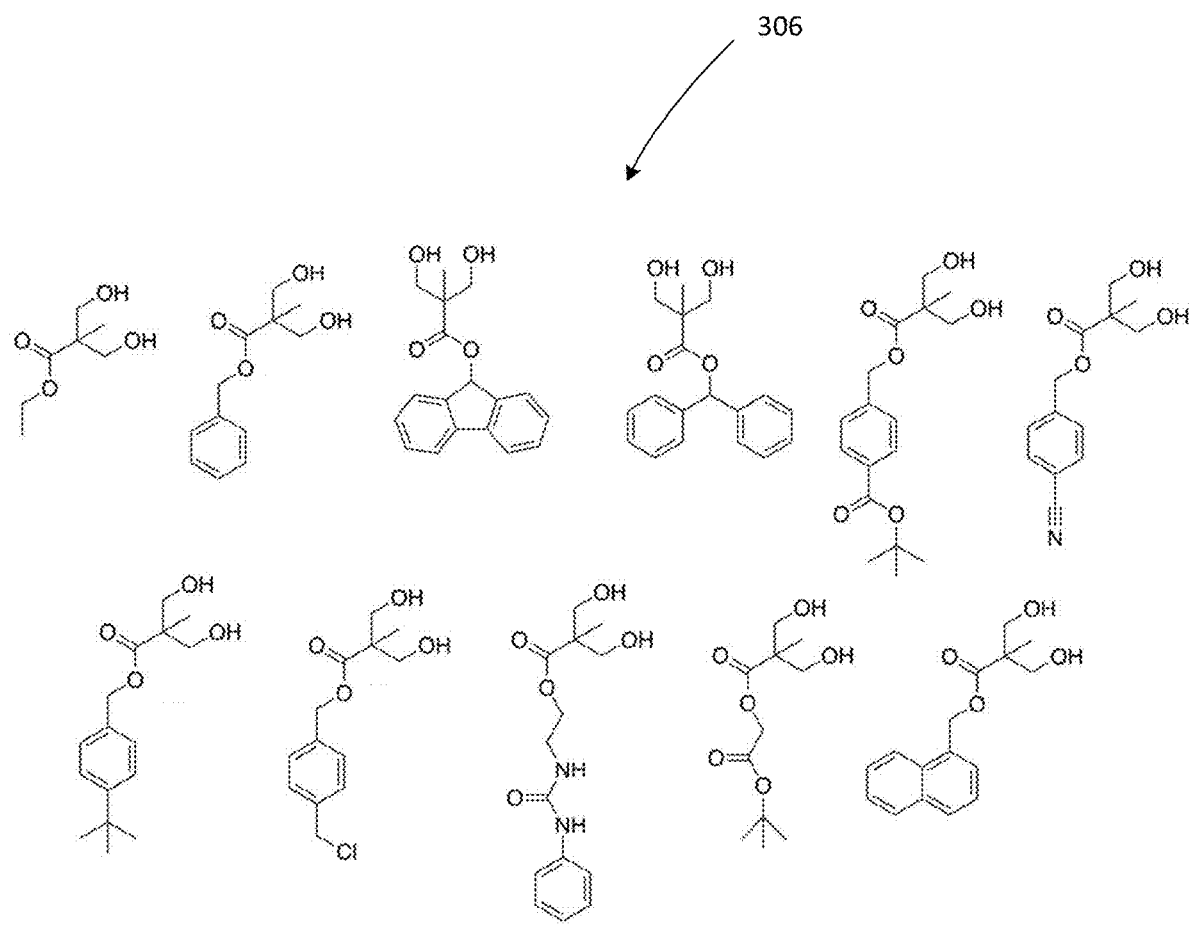
FIG. 3B illustrates a diagram of example, non-limiting functionalized diol monomers that can be synthesized by the alkylation scheme in accordance with one or more embodiments described herein.

In certain embodiments, an amount of the base relative to the substrate is between 200-350 mol %. In certain embodiments, an amount of the promoter or catalyst relative to the substrate is between 10-100 mol %. In certain embodiments, wherein a concentration of the diol is between 0.15-0.25 M. In certain embodiments, a temperature for the reaction is between −20-22° C. In certain embodiments, combining the reagents further includes using the input from the AI agent to influence an order of addition of the reagents to affect at least one of conversion, yield, and byproduct formation for the cyclic carbonate monomer synthesis. In certain embodiments, FIG. 3B illustrates a diagram of several non-limiting examples of functionalized diol monomer 306 structures that can be achieved via the alkylation scheme 300 in accordance with one or more embodiments described herein. Repetitive description of like elements employed in other embodiments described herein is omitted for sake of brevity. As shown in FIG. 3B, some exemplary functionalized diol monomer 306 structures can include, but are not limited to: MPA-benzyl ("MPA-Bn"), MPA-benzyl fluoride ("BnF$_5$"), 2-(tert-butoxy)-2-oxoethyl 3-hydroxy-2-(hydroxymethyl)-2-methylpropanoate, MPA-ethyl ("MPA-Et"), MPA-benzyl chloride ("MPA-Cl"), MPA-octyl, and/or the like. One of ordinary skill in the art will recognize that the architecture of the functionalized diol monomers 306 is not so limited; for example, additional chemical structures for the functionalized diol monomers 306 are also envisaged. As demonstrated by the exemplary structures shown in FIG. 3B, the alkylation scheme 300 can facilitate functionalization of the one or more diol monomers 302 with a wide variety of functional groups.

Figure 4A:
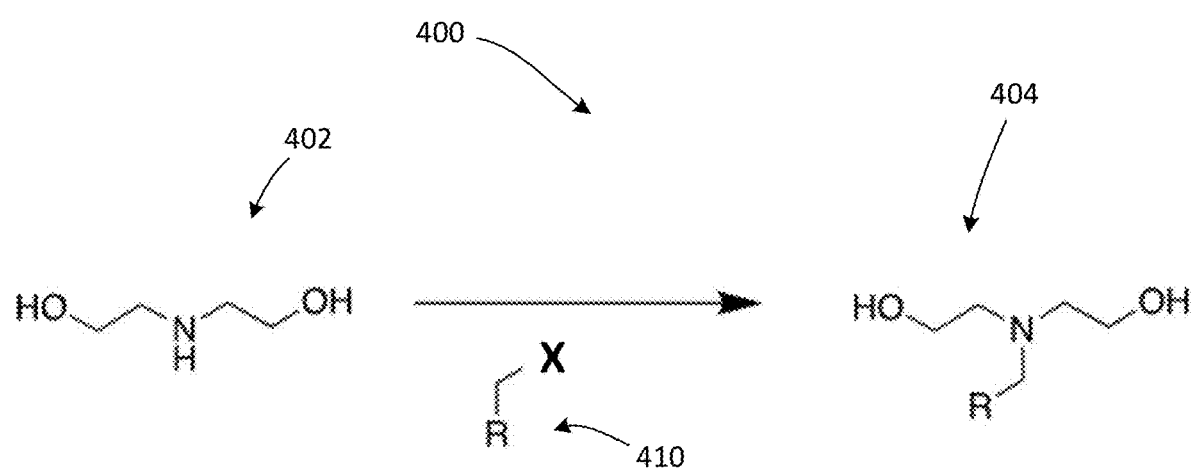
FIG. 4A illustrates a diagram of an example of a non-limiting first cyclization scheme that can be comprised within an alkylation-cyclization processes for the synthesis of cyclic carbonate monomers using N,N'-carbonyldiimidazole ("CDI") in accordance with one or more embodiments described herein.
Figure 4B:
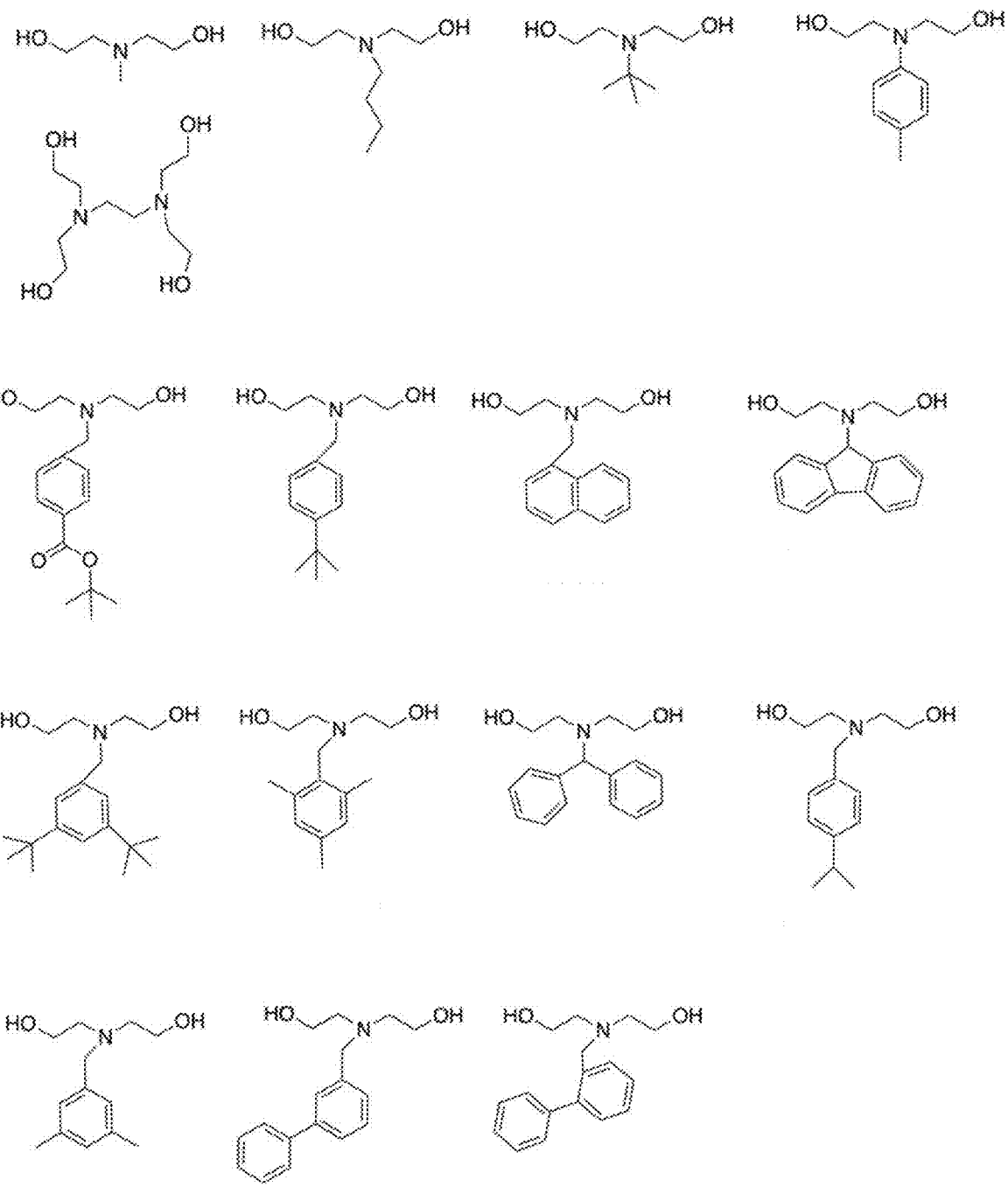
FIG. 4B illustrates a diagram of example, non-limiting functionalized cyclic carbonate monomers that can be synthesized via one or more alkylation-cyclization and/or cyclization-esterification processes in accordance with one or more embodiments described herein.

FIG. 4A depicts another exemplary alkylation scheme 400 with regards to a different type of diol monomer 402 (i.e., diethanolamine or DEA or DEAO). Alkylation scheme 400 exemplifies how the one or more diol monomers 402 can undergo an alkylation to form the one or more generic functionalized diol monomers 404 (functional 1,5-diols). For example, one or more bases can enable functionalization of the one or more diol monomers 402 with one or more substrates (e.g., functional group substrate 410) having a reactive functional group (e.g., alkyl, benzylic, or allylic halides and/or alcohols). For instance, the one or more substrates 410 having a reactive functional group (e.g., alkyl, benzylic, or allylic halides and/or alcohols) can be represented by "R—X" in FIG. 4A. FIG. 4B illustrates a diagram of example, non-limiting functionalized diol monomer 406 structures that can be achieved via the alkylation scheme 400 in accordance with one or more embodiments described herein. Repetitive description of like elements or processes employed in other embodiments (e.g., in FIGS. 3A and 3B) described herein are omitted here for sake of brevity.

Figure 5:
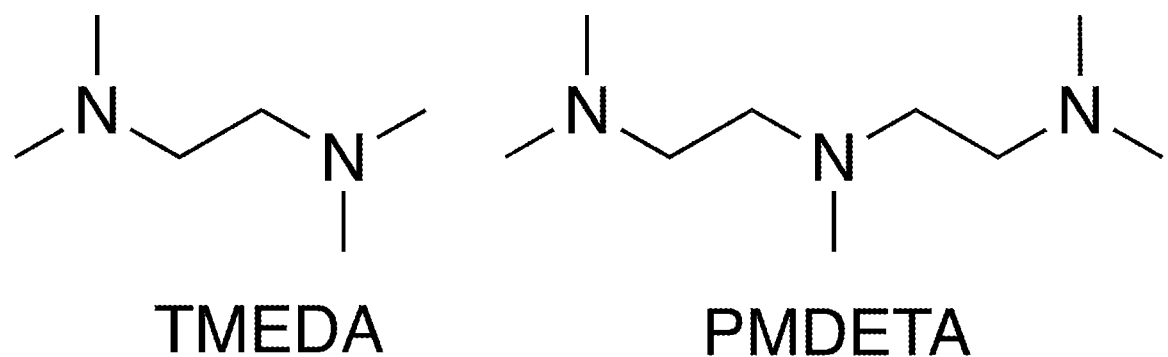
FIG. 5 illustrates a diagram of example, non-limiting bases that may be used in accordance with one or more of the cyclization schemes described herein.
Figure 5:
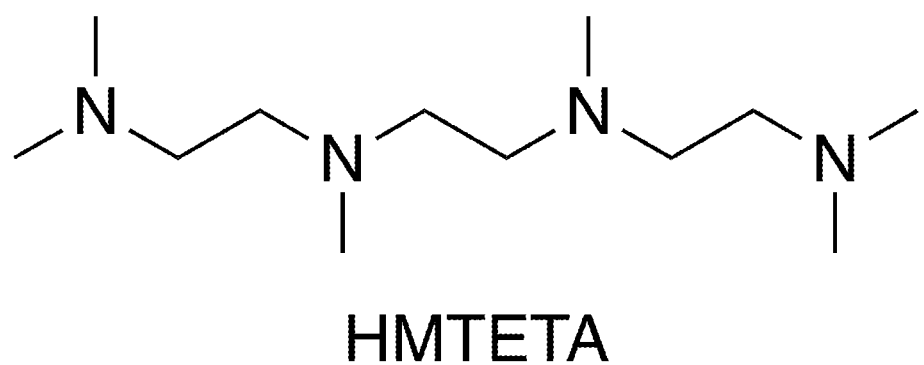

Referring now to FIG. 5, this figure illustrates a diagram of example, non-limiting bases that may be used in accordance with one or more of the cyclization schemes described herein. In general, the base may be a tertiary amine, and any may be at least one of triethylamine and diisopropylethyl amine, for example. The 1,3- and 1,5-diol substrates produced with respect to the processes described above with respect to FIGS. 3A, 3B, 4A, and 4B may each have specific challenges to ring-closing carbonate formation using $CO_2$. In certain embodiments, a base may be used that serves as both a catalyst and an acid acceptor, or as a catalyst in combination with an acid acceptor in a sequential process, together with either TsCl or MsCl, for example. In certain examples, in the generation of the 6-membered carbonates, a single base may be used to serve both purposes (i.e., as a catalyst and an acid receptor) as this may simplify an eventual automated process. In certain examples, the stoichiometry of diol to base to TsCl may be set at (1:2:1) to consistently evaluate the efficacy of the bases (24 H). In certain examples, a number of variables may be altered when converting Bn-diol ("benzyl-diol") to the cyclic form of TMC-Bn ("trimethylene carbonate benzyl") (e.g., using $CO_2$ sourced from dry ice or a cylinder, 1 atm) including reaction time, temperature, molarity, solvent, order of addition, cost of goods, and conversion of diol to carbonate without oligomerization. From this evaluation, a number of interesting observations were identified. First, TsCl provided significantly higher conversions than MsCl, the source of $CO_2$ (dry ice or cylinder) did not make a difference in the conversion, and increasing the temperature reduced the conversion. In certain experiments, the tert-amines (triethanolamine (TEA), N,N-diisopropylethylamine (DIEA)) resulted in ~25-50% conversion, stronger bases (1,8-diazabicycloundec-7-ene (DBU), triazabicyclodecene (TBD) and 1,3-benzodioxolylbutanamine (MBD)) resulted in lower yields (<40%), while nucleophilic bases (4-dimethylaminopyridine (DMAP)) produced no carbonates. In these experiments, DBU, TBD, and DIEA on a solid support resins resulted in little to no conversion to carbonate. In other examples, guanidinium and phosphonium bases provided high yields with modest oligomerization. Although these results were promising, the cost of these bases may be prohibitively high for the requisite scale of the reactions needed, and the oligomer formation may not meet certain screening criteria. However, using TMEDA as a base provided, in certain example experiments, an initial yield of 83% with no oligomerization. As such, in certain embodiments, TMEDA and related compounds are used as a base in accordance with one or more of the cyclization schemes described herein. FIG. 5 illustrates a number of example bases that may aid in yielding rapid ring-closure, limited or no side reactions, ease of purification, and near quantitative conversion. These examples include TMEDA, N,N,N',N'', N''-pentamethyldiethylenetriamine (PMDETA), and 1,1,4,7, 10,10-Hexamethyltriethylenetetramine (HMTETA). However, it should be appreciated that these bases are merely non-limiting example bases, and other bases may be used in accordance with one or more of the cyclization schemes described herein.

Figure 6A:
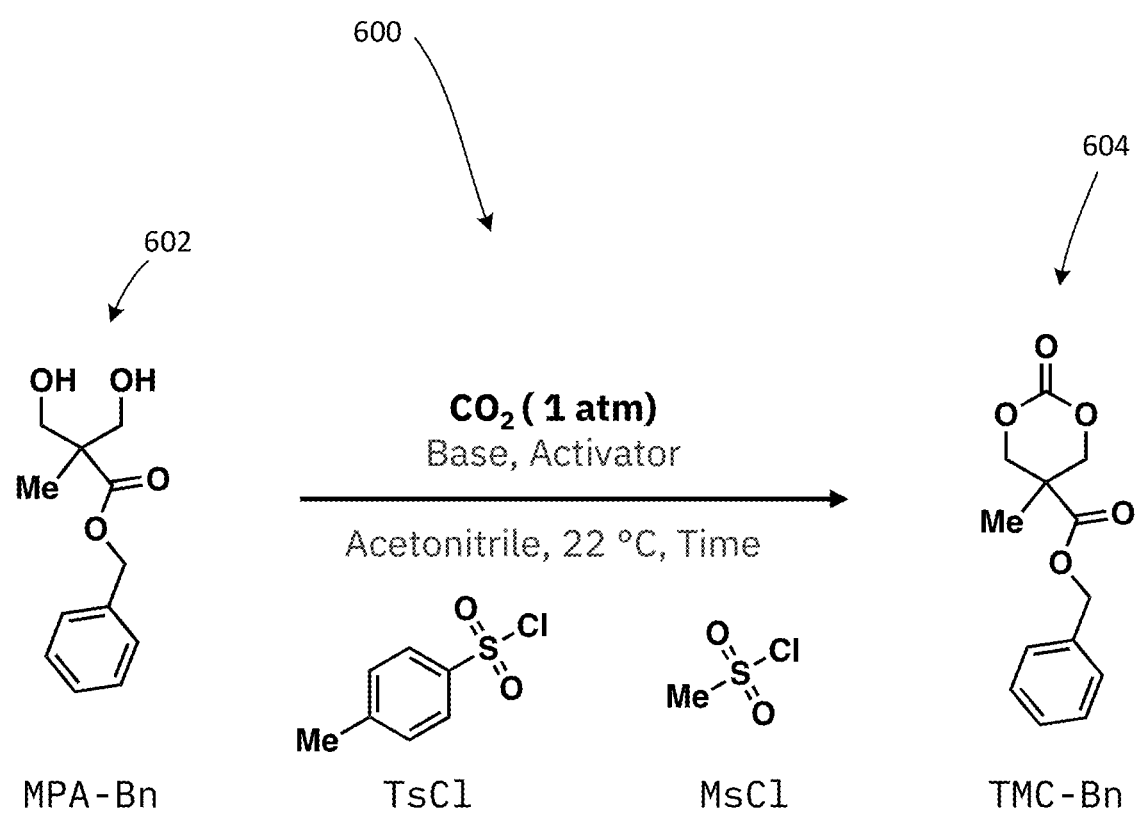
FIG. 6A illustrates a diagram of an example, non-limiting first cyclization scheme that can be comprised within an alkylation-cyclization processes for the synthesis of 6-membered cyclic carbonate monomers using tetramethylethylenediamine (TMEDA) as a base in accordance with one or more embodiments described herein.

Referring now to FIG. 6A, this figure illustrates a diagram of an example, non-limiting first cyclization scheme 600 that can be comprised within an alkylation-cyclization processes for the synthesis of 6-membered cyclic carbonate monomers using tetramethylethylenediamine (TMEDA) as a base in accordance with one or more embodiments described herein. TMEDA may exhibit one or more features related to ease of handling, low toxicity, and an ability to remove imidazole byproducts. With regard to the example of the first cyclization scheme 600 shown in FIG. 6A, MPA-Bn was selected as the functionalized diol monomer 602. In this example, the functionalized diol monomer 602 was reacted in the presence of $CO_2$, a base, an activator, acetonitrile, and either of TsCl or MsCl. The reaction temperature was about 22° C. The reaction proceeds to produce TMC-Bn as the functionalized 6-membered cyclic carbonate monomer.

Although specific reaction conditions and reagents are referred to with regard to the example reaction scheme shown in FIG. 6A, it should be appreciated that a number of reaction conditions may be varied to optimize yield, kinetics and the mitigation of oligomerization. Some of these reaction conditions may include the order of addition of reaction components, TsCl (or MsCl) stoichiometry, base stoichiometry (e.g., TMEDA stoichiometry), and the use of additional related bases. In one example experiment, using 1 equivalent of base resulted in only 50% conversion as the base was removed as a precipitated salt. In another example experiment, screening TMEDA stoichiometry and holding the diol to TsCl ratio to 1:1, higher conversions may be achieved for a TMEDA stoichiometry of 2. TsCl, which may be prone to hydrolysis to the acid, was used without further purification. In other experimental examples, the stoichiometry was varied relative to the diol and the base: holding the diol to TMEDA ratio at 1:2, and the TsCl was varied at 1, 1.25, 1.5, 1.75 and 2. In these examples, it was determined that the TsCl content (of 1.5 equivalents and above) significantly improved the conversion from 83 to 100%, by the limits of the NMR. This data suggests that possible impurities in the TsCl limited full conversion, and this may be solved with an increase in the stoichiometry of this inexpensive reagent. Moreover, in these example experiments, it should be pointed out that no oligomerization was observed by NMR.

In other example experiments with regard to the example reaction scheme shown in FIG. 6A, the order of addition of reagents was varied. In certain experiments, the TMEDA was added to TsCl and diol, the addition of TsCl to TMEDA and diol, and the addition of diol to TMEDA and TsCl all in the presence of $CO_2$ (1 ATM). Holding the conditions of diol: TMEDA: TsCl to 1:2;1.5 showed minimal difference in conversion rates.

In other example experiments with regard to the example reaction scheme shown in FIG. 6A, the stoichiometry of diol to base to TsCl was set at (1:2:1) to evaluate the kinetics of TMEDA and related compounds at 0° C. in acetonitrile in the presence of $CO_2$ (1 ATM). Interestingly, high conversions were achieved within 10 min with no oligomerization. The speed of this reaction, robustness of the chemistry and efficacy may afford the opportunity for automation. Initial studies demonstrated feasibility in a CSRT reactor with an average resonance time of 10 min with a yield of about 86%.

Upon completion of the reaction scheme shown in FIG. 6A, the acetonitrile (can) was removed, and several methods to isolate and purify the TMC-Bn were investigated. In certain embodiments, the methods to isolate and purify the TMC-Bn include automated column, filtration through a plug of silica gel followed by recrystallization, and an aqueous workup (1M HCl, brine) followed by recrystallization. The purification may be complicated by any excess reagents and the relatively nonpolar Ts-salts. Using the automated column with a UV detector using a gradient solvent system with hexane/ethyl acetate (80/20 to 30/70), the Ts-salts were able to be detected and removed. In certain examples, the final product may still need to be recrystallized. Filtration through a plug of silica gel may be used to remove most of the excess reagents, but significant Ts-salts may still be present. These salts may be removed by crystallization, but the salts may co-crystallize with the TMC-Bn, requiring recrystallization. Aqueous extraction was also surveyed as a means to isolate TMC-Bn followed by recrystallization (ethyl acetate/hexane).

Figure 6B:
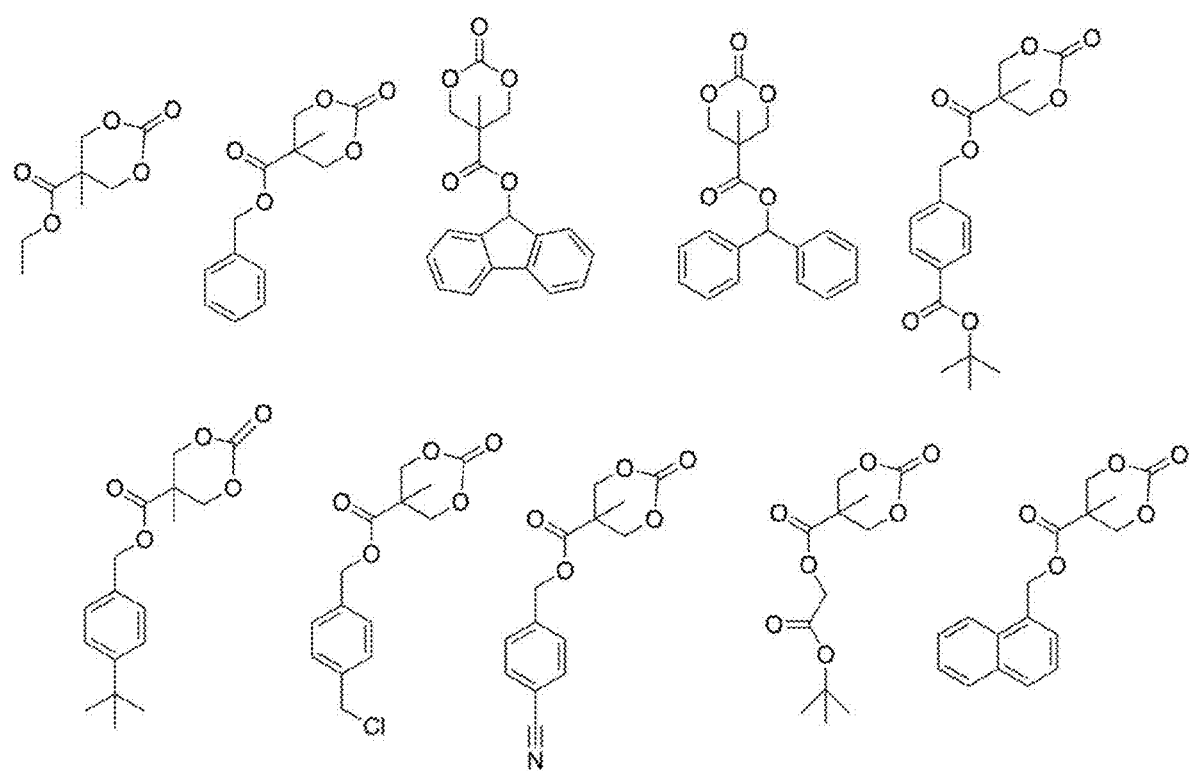
FIG. 6B illustrates a diagram of example, non-limiting functionalized 6-membered cyclic carbonate monomers that can be synthesized via one or more alkylation-cyclization and/or cyclization-esterification processes in accordance with one or more embodiments described herein.

Referring now to FIG. 6B, this figure illustrates a diagram of an example, non-limiting functionalized 6-membered cyclic carbonate monomers that can be synthesized via one or more alkylation-cyclization and/or cyclization-esterification processes (e.g., first cyclization scheme 600) in accordance with one or more embodiments described herein. In addition to the TMC-Bn, FIG. 6B illustrates a number of additional cyclic carbonates. In certain example reaction schemes to product these cyclic carbonates, the reactions were carried out in AcN either at 0° C. or RT (1 h). The solutions were concentrated, dissolved in ethyl acetate and extracted with 1M HCl and brine, and recrystallized (ethyl acetate/hexane) without heating to mitigate unwanted ring-opening. A diverse range of monomers were prepared by the installation of functional groups that were either hydrophobic or hydrophilic, contained protected functional groups such as an acid, functional groups for post-polymerization modification as well as bulky aromatic groups to be used as structure-directing agents in the eventual formation of block polymers and micelles. Installation of functional groups at the distal 5-position is optimal for subsequent polymerization. Repetitive description of like elements employed in other embodiments described herein is omitted for sake of brevity. One of ordinary skill in the art will recognize that the structures depicted in FIG. 6B demonstrate exemplary monomers that can be formed in accordance with the methods, alkylation-cyclization processes, and/or cyclization-esterification processes described herein. However, the variety of monomers that can be synthesized via the methods, alkylation-cyclization processes, and/or cyclization-esterification processes described herein is not limited to the exemplary structures depicted in FIG. 6B. Moreover, it should be appreciated that the specific reaction conditions described above with respect to FIG. 6A is only one example, and the reaction reagents and conditions may be modified in any suitable manner.

Figure 7A:
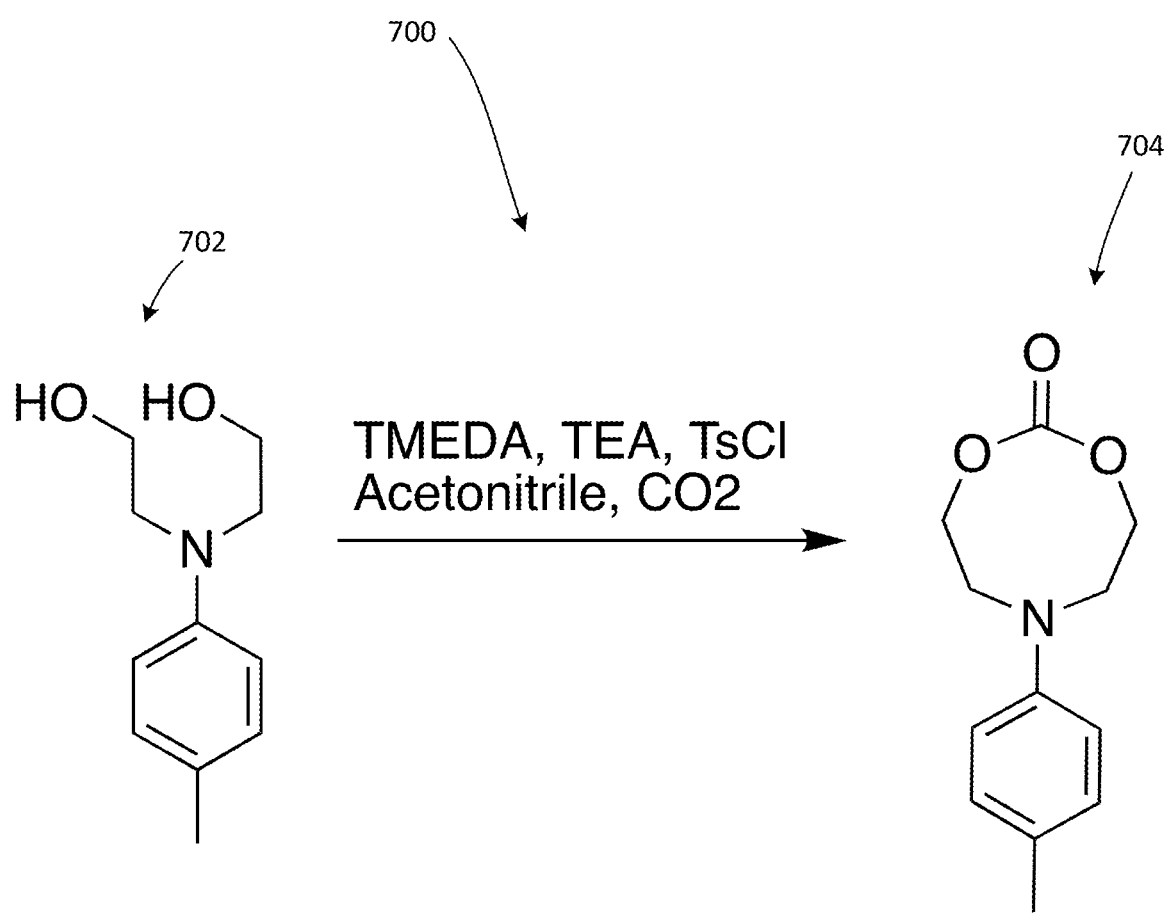
FIG. 7A illustrates a diagram of an example, non-limiting first cyclization scheme that can be comprised within an alkylation-cyclization processes for the synthesis of 8-membered cyclic carbonate monomers using tetramethylethylenediamine (TMEDA) as a base in accordance with one or more embodiments described herein.

Referring now to FIG. 7A, this figure illustrates a diagram of an example, non-limiting second cyclization scheme that can be comprised within an alkylation-cyclization process for the synthesis of 8-membered cyclic carbonate monomers using tetramethylethylenediamine (TMEDA) as a base, in accordance with one or more embodiments described herein. As previously mentioned, the 1,3- and 1,5-diols may possess certain challenges to achieving ring closure, and the tert-amine group in 1,5-diol may present a particular one of these challenges. When applying the synthetic procedure described above in FIGS. 6A and 6B for the 1,3-diols (e.g., diol:TMEDA:TSCl 1:2:1.5) to the 1,5-diols, the monomer itself salted out, limiting the yield and complicating monomer isolation. In certain embodiments, instead of running the reaction in excess TMEDA, an additional base is used in combination with the TMEDA (e.g., triethylamine (TEA) 3.5-4 equivalents). In this way, side reactions to the monomer may be minimized, and more importantly, TEA-Ts salts are considerably less soluble than TMEDA-Ts salts, mitigating isolation, and purification issues. Moreover, TMEDA can be used as a catalyst instead of both catalyst and base to further reduce Ts-salts. In certain example experiments, two conditions were explored, including diol:TMEDA:TEA:TsCl (1:2:3.5:1.5 and 1:0.35:3.5:1.5) in AcN (0° C.), where the bases were added dropwise to a solution of diol and TsCl. In both cases, the consumption of alcohol was high to what looked to be like two carbonate peaks in the NMR (~4.05 and ~4.2) but not associated with oligomerization. It may be possible that this erroneous NMR peak may be due to the presence of larger cyclics, as the base was dropped into excess diol that could possibly dimerize. To test this hypothesis and mitigate this side reaction, the diol was added dropwise to a solution of bases and TsCL and followed by NMR. Near quantitative conversion of diol to cyclic 8-membered carbonate was observed, irrespective of the TMEDA content.

With regard to the second cyclization scheme of FIG. 7A, upon completion of the reaction, the AcN was removed, and the compound was dissolved in chloroform and purified by an automated gradient column (hexane/ethyl acetate (80/20 to 30/70)) or filtration through a plug of silica (hexane/ethyl acetate (70/30), followed by recrystallization (ethyl acetate/hexane). In general, the isolated yields with the automated column purification were in the 80-85% range, while the plug filtration followed by recrystallization was in the 50-55% range.

Figure 7B:
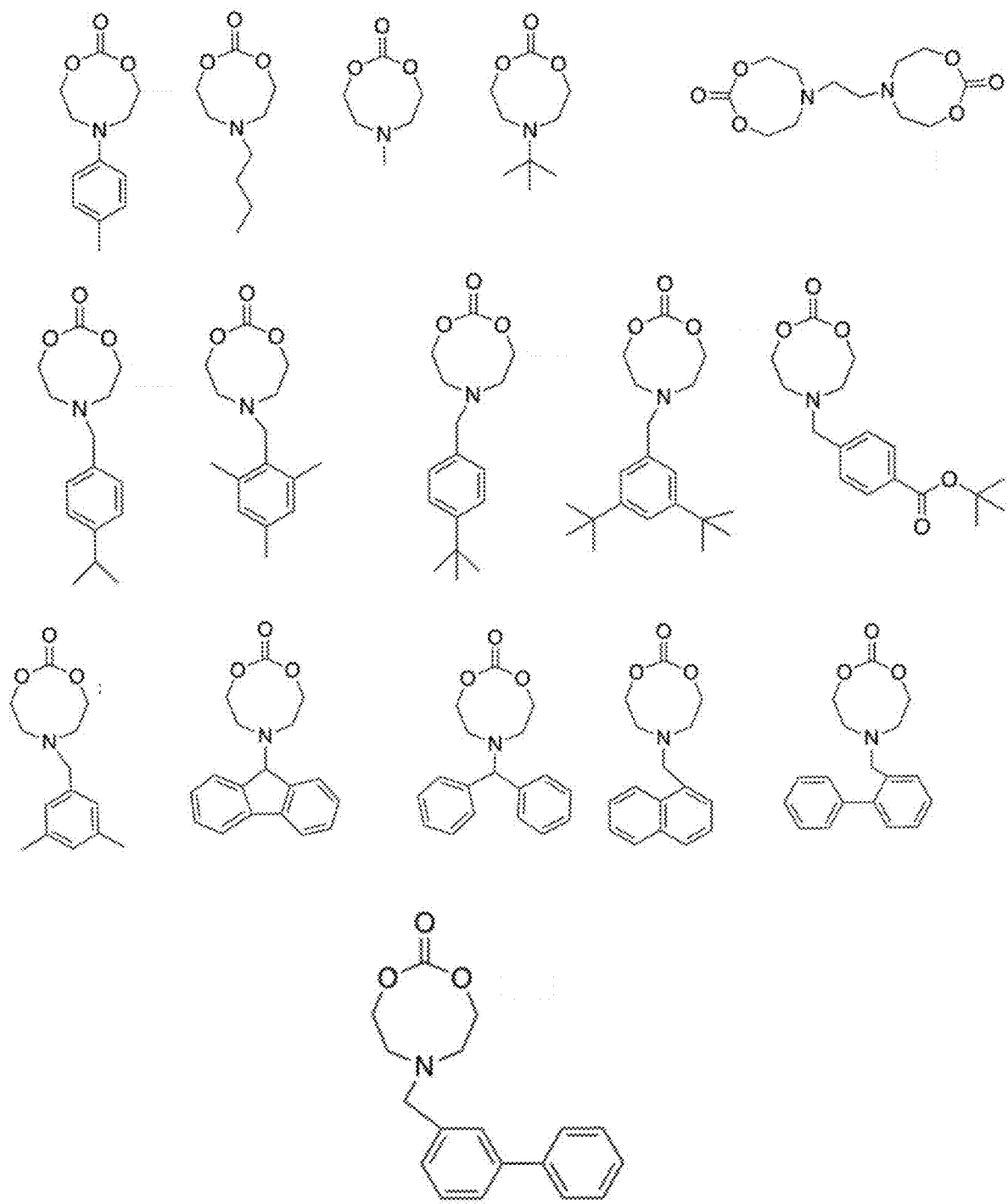
FIG. 7B illustrates a diagram of example, non-limiting functionalized 8-membered cyclic carbonate monomers that can be synthesized via one or more alkylation-cyclization and/or cyclization-esterification processes in accordance with one or more embodiments described herein.

Referring now to FIG. 7B, this figure illustrates a diagram of an example, non-limiting functionalized 8-membered cyclic carbonate monomers that can be synthesized via one or more alkylation-cyclization and/or cyclization-esterification processes (e.g., the second cyclization scheme 700) in accordance with one or more embodiments described herein. This general procedure of the second cyclization scheme was applied to the diols described above and illustrated in FIG. 4B, to generate the library of 8-membered cyclic carbonates shown in FIG. 7B. Significant structural diversity was introduced to this monomer platform that will eventually allow both homo- and block polymers with distinctive properties. The robustness of the chemistry and efficacy of the transformation affords the opportunity of automation, and initial studies demonstrated feasibility in a CSRT reactor with an average resonance time of 10 min with a yield of nearly 100%. One of ordinary skill in the art will recognize that the structures depicted in FIG. 7B demonstrate exemplary monomers that can be formed in accordance with the methods, alkylation-cyclization processes, and/or cyclization-esterification processes described herein. However, the variety of monomers that can be synthesized via the methods, alkylation-cyclization processes, and/or cyclization-esterification processes described herein is not limited to the exemplary structures depicted in FIG. 7B. Moreover, it should be appreciated that the specific reaction conditions described above with respect to FIG. 7A is only one example, and the reaction reagents and conditions may be modified in any suitable manner.

In certain embodiments, as a means to expedite and streamline an automated process of monomer synthesis, the two-step reaction to the carbonate monomer described herein may be telescoped (i.e., sequential reactions without isolation and purification of the first transformation). With regard to telescoping, the 6-membered carbonate synthesis of TMC-Bn, Bis MPA, DIEA, and benzyl bromide were charged (diol:BnBr:DIEA 1:1:1) into a flask and dissolved in AcN (90° C., 30 min), where the reaction was followed by NMR, and judged complete by the shift in the benzyl protons (>95% conversion by NMR, <30 min). The functional diol was directly added to a flask containing TsCl (1:1.5) dissolved in AcN. The reaction was cooled (0° C.), charged with $CO_2$, and TMEDA (2eq.) was added dropwise ~15 min and allowed to go for 1h. Full conversion of diol to carbonate was observed (NMR). The reaction was placed directly into a separatory funnel containing 300 mls of ethyl acetate and extracted 2× with 1M HCl and 1× brine, followed by recrystallization (ethyl acetate/hexane). Isolated yields on multiple reactions consistently ranged from 60-70% over the two-step process. To further demonstrate the applicability of this telescoped process, bis MPA, DIEA, and pentafluoro benzyl bromide were charged into a flask and reacted for 45 min at 90° C. The reaction was placed into a reaction flask with TsCl (1:1.5) dissolved in AcN, where TMEDA (2eq), dissolved in AcN, was added dropwise in the presence of $CO_2$. After an aqueous workup and recrystallization from ethyl acetate/hexane provided white crystals in 50% yield.

To demonstrate the feasibility of this telescoping process for 8-membered carbonates, diethyanolamine, benzyl bromide and $k_2CO_3$ (1:0.95:excess) were charged into a flask (90° C.). Near quantitative conversion to the substituted diol was observe in one hour. The reaction was cooled, filtered into an addition funnel to a flask containing TsCl, TMEDA and TEA (1.5:0.35:3.5) dissolved in AcN (0° C.). The flask was flushed with $CO_2$ and the diol was added dropwise over a 15 min and allowed to react for an additional 30 min and followed by NMR. Unlike the sequential process where the first step is purified, the telescoped procedure showed oligomer formation. It may be possible that the $k_2CO_3$ led to the oligomerization, and to that end, $k_2CO_3$ was replaced with potassium phosphate tribasic (PPB) (diol:BnBr:PPB1: 1:excess) that led to near quantitative conversion of diol to carbonate, where the PPB and related salts could be easily removed by filtration. The subsequent telescope reaction TsCl, TMEDA and TEA (1.5:0.35:3.5) led to near quantitative conversions to diol and cyclic carbonate, respectively, without oligomerization. The reproducibility of this process was further demonstrated in a second example with a functional monomer, where the diol was synthesized by reaction of diethanolamine (DIEA), pentafluoro benzyl bromide and PPB (diol:BnF$_5$Br:DIEA 1:1:excess), quatitative conversion to diol by NMR, followed by its addition to an addition funnel to a flask containing TsCl, TMEDA and TEA (1.5:0.35:3.5) dissolved in AcN (0° C.) under CO$_2$, that led to near quantitative conversion of diol to carbonate as confirmed by NMR.

In certain examples of the present embodiments, subsequent optimization of the reaction conditions (e.g., with user input and/or with the assistance of an AI neural network system capable of assisting with the generation of libraries of functional 6- and 8-membered cyclic carbonate monomers using CO$_2$) brought the reaction time down to about 10 min (e.g, at a temperature of 90° C.), and the optimized process was demonstrated in a semi-automated continuous stirred tank reactor (CSTR) with an average resonance time of about 10 min.

Figure 8:
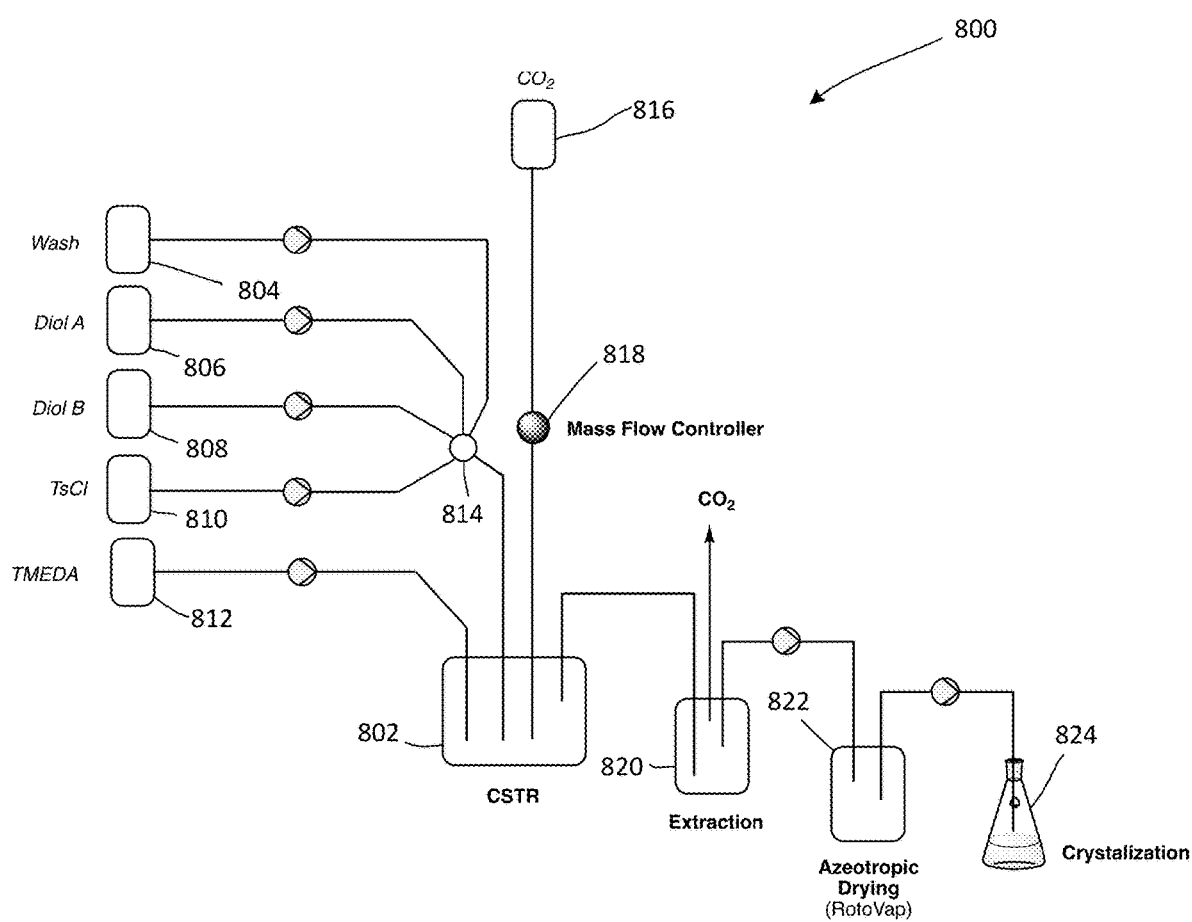
FIG. 8 is a schematic diagram illustrating an example reactor for performing the cyclization reactions of one or more of the embodiments described herein.

Referring now to FIG. 8, a schematic diagram is shown of an example reactor 800 for performing the cyclization reactions of one or more of the embodiments described herein. As shown in FIG. 8, the reactor 800 includes a CSTR 802 for stirring the reaction components. The reactor 800 also includes several material input mechanisms 804, 806, 808, 810, 812 and 816 for introducing one or more reaction components (e.g., wash, diol A, diol B, TaCl, TMEDA, CO$_2$, etc.). The amounts and rates at which the reaction components are introduced into the CSTR 802 may be controlled by one or more valves 814 and/or mass flow controllers 818. In certain embodiments, the reaction products may be transferred from the CSTR 802 to an extraction unit 820. In certain embodiments, CO$_2$ may be removed from the extraction unit 820. In certain embodiments, certain of the reaction components may be transferred from the extraction unit 820 to a drying unit 822, and from there to a crystallization unit 824. It should be appreciated that the reactor 800 configuration is merely one example, and any suitable reactor configuration may be used to automate the process of performing the cyclization reactions and extractions. It should be appreciated that other reactor components such as pumps, temperature controllers, separators, distillation columns, mixers, valves etc. are contemplated within the scope of the reactor design.

Figure 9:
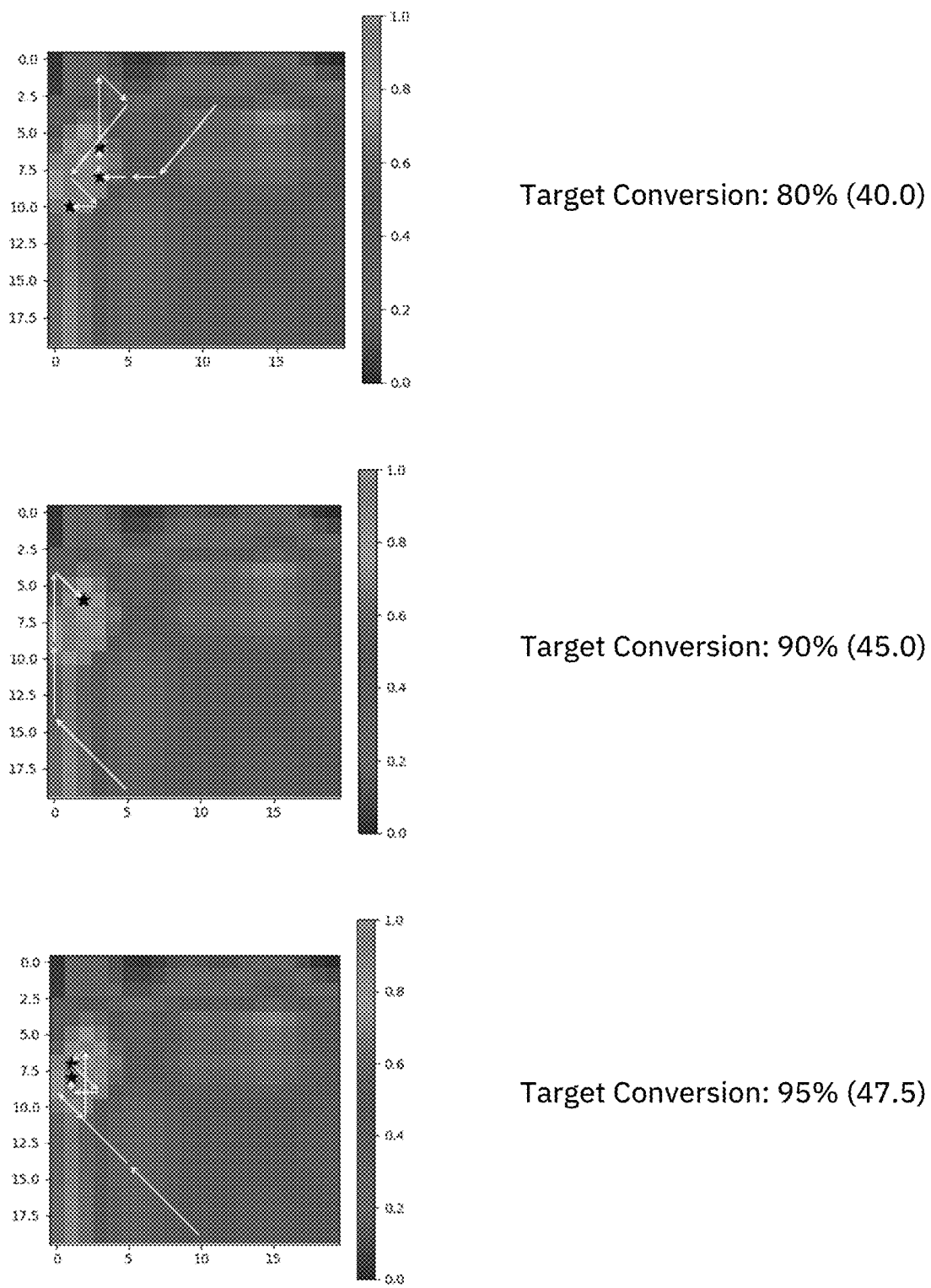
FIG. 9 illustrates examples of a visual output of a reinforcement learning agent of a neural network that is moving over a continuous representation of bases shown as a 2D landscape.

In some embodiments, one or more computer systems 100 may operate using one or more machine learning or artificial intelligence techniques described herein with respect to a neural network 200, and may operate to perform machine-learning surveys of reaction conditions for reinforcement learning. As discussed above, one or more key reaction condition variables (e.g., reaction temperature, reaction time, monomer: oligomer ratio, cost of reagents, cost of catalysts, molarity, order of addition, type of catalyst, type of base, yields, conversion rates, etc.) may be inputted to the neural network 200 and used in conjunction with one or more computer systems to create a model for optimizing the reaction conditions. Referring now to FIG. 9, this figure shows examples of a visual output of a reinforcement learning agent of the neural network 200 that is moving over a continuous representation of bases shown as a 2D landscape, where the color (i.e., the greyscale of the pixels) represents a degree of conversion with a corresponding base. In certain embodiments, one or more machine learning or artificial intelligence techniques described herein with respect to a neural network 200 may be utilized in a process including running experiments, compiling results of the experiments in a database (e.g., data stored in the memory 120 of the computer system 100), performing reinforcement learning that is augmented with density functional theory (DFT) calculations, and performing catalyst/reaction condition predictions (i.e., that are optimized for reaction yield, kinetics, minimal by-products etc.). In certain embodiments, a computer implemented method for training an AI agent for cyclic carbonate monomer synthesis from carbon dioxide includes pretraining a synthesis model with an AI agent based on historical monomer synthesis data. These method may also include selecting, based on the synthesis model, reagents to synthesize the cyclic carbonate monomer, identifying, based on the synthesis model, an experimental synthesis protocol. These method may also include selecting, based on the synthesis model, process operations for the cyclic carbonate monomer synthesis, executing the experimental synthesis protocol to generate the cyclic carbonate monomer, and collecting characterization data of results of the cyclic carbonate monomer synthesis for retraining of the synthesis model.

Certain features of the present embodiments may allow for rapid ring closure, no side reactions, easy purification, near quantitative conversion, and may be broadly applicable to 1,3-diols and 1,5-diols.

Reference in the specification to "one embodiment" or "an embodiment," as well as other variations thereof, means that a particular feature, structure, characteristic, and so forth described in connection with the embodiment is included in at least one embodiment. Thus, the appearances of the phrase "in one embodiment" or "in an embodiment," as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

The descriptions of the various embodiments have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for synthesizing a cyclic carbonate monomer using carbon dioxide ($CO_2$), the method comprising:
   combining reagents to synthesize the cyclic carbonate monomer, the reagents including
   a substrate that is a 1,X-diol, where X is between 2 and 5,
   a first base that is a tertiary amine,
   a promoter that is a second base that is a multidentate, bis-tertiary amine where nitrogens are separated by 2 to 4 carbon atoms, the second base being different than the first base,
   a solvent,
   at least one of TsCl and MsCl, and $CO_2$,
   wherein the substrate includes a reactive functional group, and the method further comprises reacting the substrate with the first base to promote generation of a functionalized diol monomer that is selected from the group consisting of

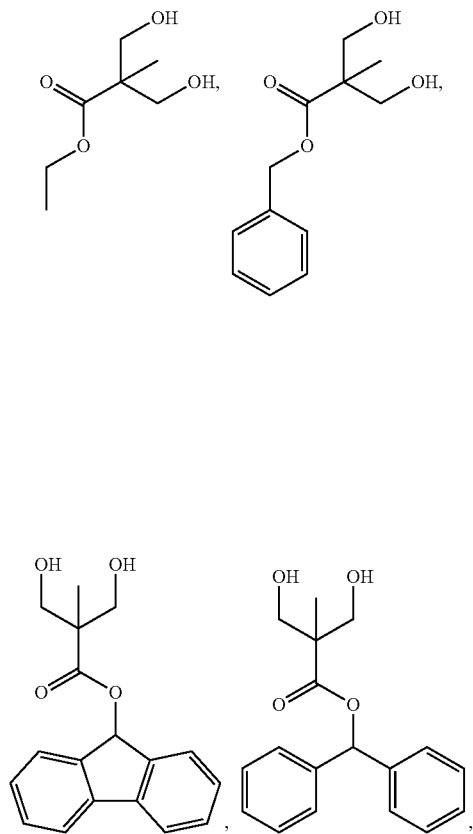

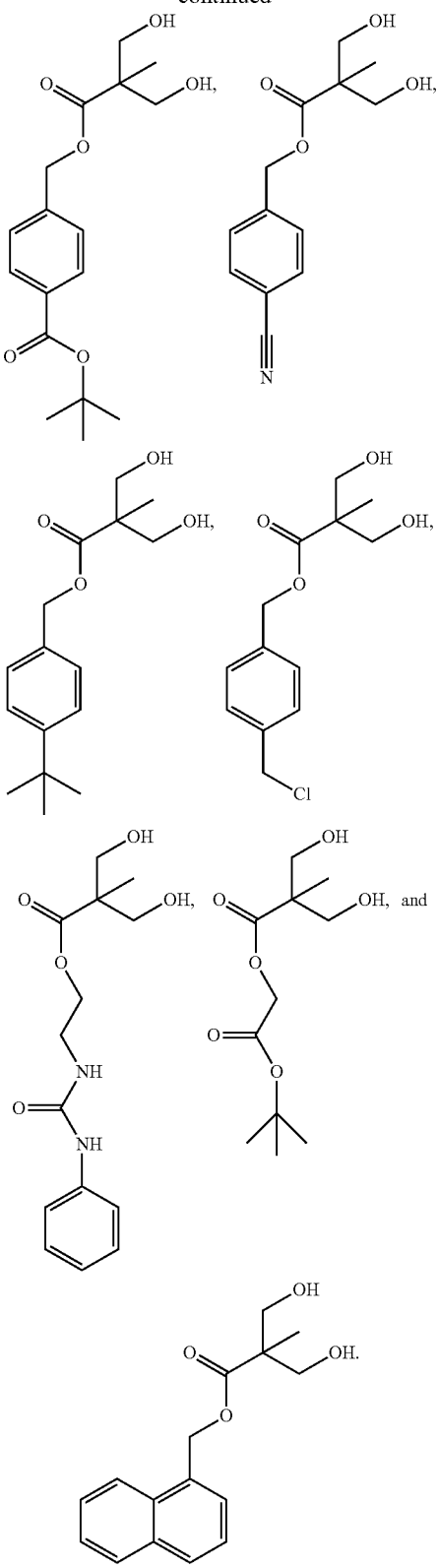

2. The method of claim 1, wherein the first base is at least one of triethylamine and diisopropylethyl amine.

3. The method of claim 1, wherein the promoter is selected from the group consisting of

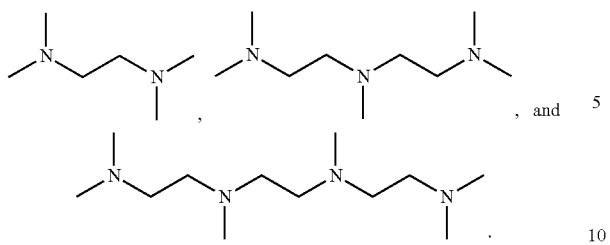

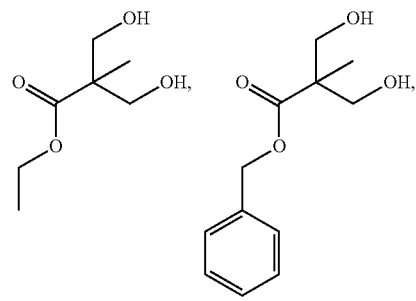

4. The method of claim 1, wherein the solvent includes at least one selected from the group consisting of acetonitrile, ethyl acetate, tetrahydrofuran, dimethylformamide, and dimethyl sulfoxide.

5. The method of claim 1, wherein an amount of the first base relative to the substrate is between 200-350 mol %.

6. The method of claim 1, wherein an amount of the promoter relative to the substrate is between 10-100 mol %.

7. The method of claim 1, wherein a concentration of the diol is between 0.15-0.25 M.

8. The method of claim 1, wherein a reaction temperature is between −20-22° C.

9. The method of claim 1, further comprising identifying a cyclic carbonate monomer to synthesize based on input from an artificial intelligence (AI) agent, wherein combining the reagents further includes using the input from the AI agent to influence an order of addition of the reagents to affect at least one of conversion, yield, and byproduct formation for the cyclic carbonate monomer synthesis.

10. A computer implemented method for training an AI agent for cyclic carbonate monomer synthesis from carbon dioxide, comprising:
pretraining a synthesis model with an AI agent based on historical monomer synthesis data;
selecting, based on the synthesis model, reagents to synthesize a cyclic carbonate monomer, the reagents including
a substrate that is a 1,X-diol, where X is between 2 and 5,
a first base that is a tertiary amine,
a promoter that is a second base that is a multidentate, bis-tertiary amine where nitrogens are separated by 2 to 4 carbon atoms, the second base being different than the first base,
a solvent,
at least one of TsCl and MsCl, and
CO$_2$;
identifying, based on the synthesis model, an experimental synthesis protocol;
selecting, based on the synthesis model, process operations for the cyclic carbonate monomer synthesis;
executing the experimental synthesis protocol to generate the cyclic carbonate monomer; and
collecting characterization data of results of the cyclic carbonate monomer synthesis for retraining of the synthesis model,
wherein the substrate includes a reactive functional group, and the method further comprises reacting the substrate with the first base to promote generation of a functionalized diol monomer that selected from the group consisting of

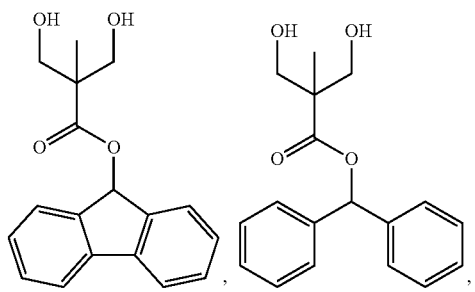

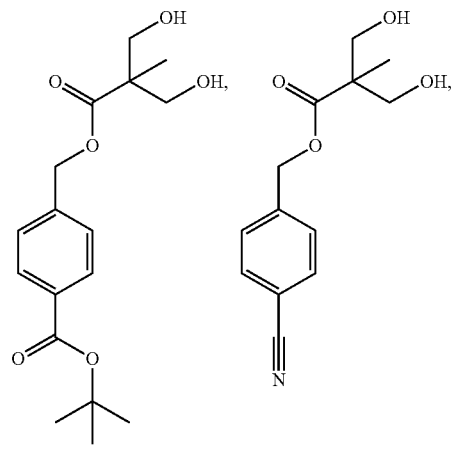

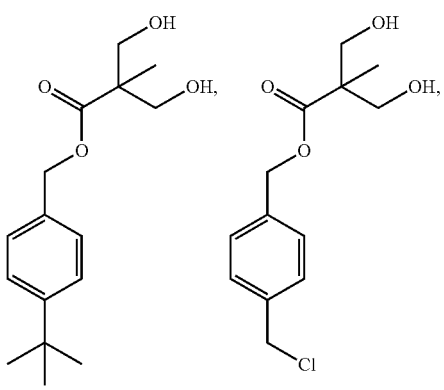

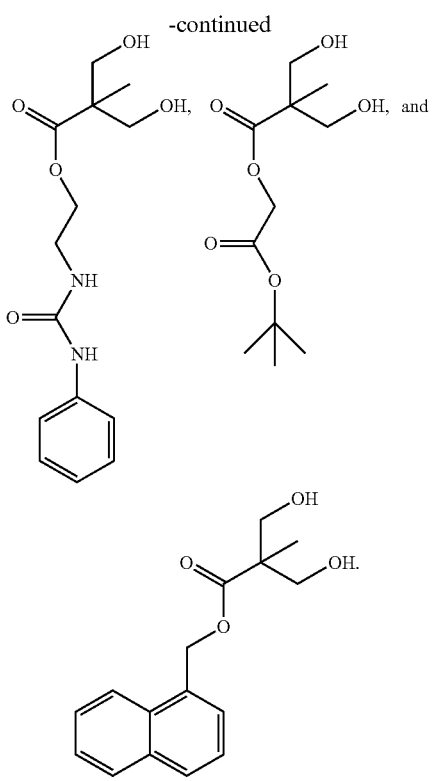

11. The method of claim 10, further comprising retraining the synthesis model based on the characterization data.

12. The method of claim 10, wherein the first base is at least one of triethylamine and diisopropylethyl amine.

13. The method of claim 10, wherein the promoter is selected from the group consisting of 14. The method of claim 10, wherein the solvent includes at least one selected from the group consisting of acetonitrile, ethyl acetate, tetrahydrofuran, dimethylformamide, and dimethyl sulfoxide.

15. The method of claim 10, wherein executing the experimental synthesis protocol includes using input from the synthesis model to influence an order of addition of the reagents to affect at least one of conversion, yield, and byproduct formation for the cyclic carbonate monomer synthesis.

* * * * *